US010869493B2

(12) United States Patent
Reichelt et al.

(10) Patent No.: US 10,869,493 B2
(45) Date of Patent: *Dec. 22, 2020

(54) REDUCED-SWEETENER PRODUCTS, FLAVORING MIXTURES FOR SAID REDUCED-SWEETENER PRODUCTS AND PROCESS FOR THE PRODUCTION OF PRODUCTS OF THIS TYPE

(71) Applicant: SYMRISE AG, Holzminden (DE)

(72) Inventors: Katharina Reichelt, Rosenheim (DE); Jakob Peter Ley, Holzminden (DE); Petra Hoffmann-Lücke, Delligsen (DE); Maria Blings, Holzminden (DE); Susanne Paetz, Höxter (DE); Thomas Riess, Holzminden (DE)

(73) Assignee: SYMRISE AG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/815,212

(22) Filed: Mar. 11, 2020

(65) Prior Publication Data
US 2020/0205445 A1 Jul. 2, 2020

Related U.S. Application Data

(63) Continuation of application No. 12/871,303, filed on Aug. 30, 2010, now Pat. No. 10,624,372.

(60) Provisional application No. 61/237,866, filed on Aug. 28, 2009.

(51) Int. Cl.
A23L 2/60 (2006.01)
A23G 4/06 (2006.01)
A23G 1/32 (2006.01)
A23G 3/48 (2006.01)
A23G 1/48 (2006.01)
A23G 9/42 (2006.01)
A61K 36/185 (2006.01)
A23G 9/32 (2006.01)
A23G 3/36 (2006.01)
A23L 27/30 (2016.01)
A23L 7/10 (2016.01)
A23L 27/60 (2016.01)

(52) U.S. Cl.
CPC .................. A23L 2/60 (2013.01); A23G 1/32 (2013.01); A23G 1/48 (2013.01); A23G 3/36 (2013.01); A23G 3/48 (2013.01); A23G 4/06 (2013.01); A23G 4/068 (2013.01); A23G 9/32 (2013.01); A23G 9/42 (2013.01); A23L 7/10 (2016.08); A23L 27/30 (2016.08); A23L 27/63 (2016.08); A61K 36/185 (2013.01)

(58) Field of Classification Search
CPC ............ A23L 1/21; A23L 1/28; A61K 31/365
USPC .................. 514/470; 426/538, 655
See application file for complete search history.

(56) References Cited

U.S. PATENT DOCUMENTS

| 7,332,522 | B2 | 2/2008 | Sakai et al. | |
| 7,521,079 | B2* | 4/2009 | Sakai | A61K 36/185 |
| | | | | 426/433 |
| 8,679,461 | B2* | 3/2014 | Ley | A61K 8/498 |
| | | | | 424/49 |
| 9,445,606 | B2* | 9/2016 | Krammer | A23L 33/20 |
| 2002/0188019 | A1 | 12/2002 | Ley et al. | |
| 2004/0122085 | A1* | 6/2004 | Sakai | C07D 307/88 |
| | | | | 514/470 |
| 2004/0161524 | A1* | 8/2004 | Sakai | A23K 10/30 |
| | | | | 426/655 |
| 2006/0188591 | A1 | 8/2006 | Buchholz et al. | |
| 2008/0220140 | A1* | 9/2008 | Ley | A23L 27/88 |
| | | | | 426/538 |

FOREIGN PATENT DOCUMENTS

| DE | 102004041496 A1 | 3/2006 |
| EP | 1291342 A1 | 3/2003 |
| EP | 2006067120 A1 | 7/2008 |
| EP | 1955601 A1 | 8/2008 |
| EP | 1972203 A1 | 9/2008 |
| EP | 1989944 A1 | 11/2008 |
| JP | 11253128 A | 9/1999 |
| WO | WO-2004050069 A1 | 6/2004 |
| WO | WO-2004078302 A1 | 9/2004 |
| WO | WO-2005020721 A1 | 3/2005 |
| WO | WO-2005/041684 A2 | 5/2005 |
| WO | WO-2005096841 A1 | 10/2005 |
| WO | WO-2006/003107 A1 | 1/2006 |
| WO | WO-2006058893 A2 | 6/2006 |
| WO | WO-2006106023 A1 | 10/2006 |

(Continued)

OTHER PUBLICATIONS

Kinghorn, A.D. and C.M. Compadre, "Less Common High-Potency Sweeteners," Food Sci. Technol. (N.Y.) 112 (Alternative Sweeteners): pp. 209-233.

(Continued)

Primary Examiner — Walter E Webb
(74) Attorney, Agent, or Firm — Polsinelli PC

(57) ABSTRACT

A flavoring mixture, comprising
(i) one or more sweet-tasting substances, selected from the group of naturally occurring sweet-tasting substances and the physiologically compatible salts thereof without phyllodulcin and the physiologically compatible salts thereof, and
(ii) phyllodulcin and/or one or more of the physiologically compatible salts thereof,
wherein the ratio of the sucrose equivalence of the concentration of the substance or substances of group (i) to the sucrose equivalence of the concentration of the substance or substances of group (i) is ≥2.

20 Claims, 1 Drawing Sheet

(56) References Cited

FOREIGN PATENT DOCUMENTS

| | | |
|---|---|---|
| WO | WO-2007003527 A1 | 1/2007 |
| WO | WO-2007014879 A1 | 2/2007 |
| WO | WO-2007045566 A1 | 4/2007 |
| WO | WO-2007107596 A1 | 9/2007 |
| WO | WO-2007121604 A2 | 11/2007 |
| WO | WO-2008046895 A1 | 4/2008 |

OTHER PUBLICATIONS

"Position of the American Dietetic Association: Use of Nutritive and Nonnutritive Sweeteners," Journal of the American Dietetic Association, 2004, vol. 104, No. 2, pp. 255-275.
Crosby, G.A., "New Sweeteners," Critical Reviews in Food Science and Nutrition, 1976, pp. 297-323.
Bashir et al., "The antioxidant activity of Phloretin: the disclosure of a new antioxidant pharmacorphore in flavonoids," Biochemical and Biophysical Research Communications 295, 2002, pp. 9-13.

* cited by examiner

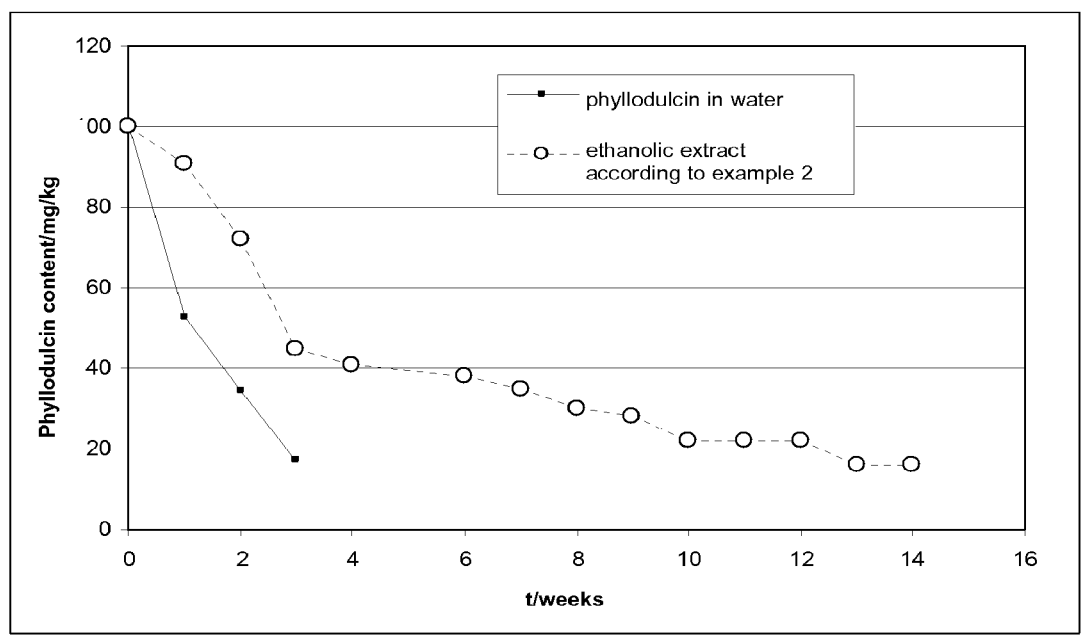

REDUCED-SWEETENER PRODUCTS, FLAVORING MIXTURES FOR SAID REDUCED-SWEETENER PRODUCTS AND PROCESS FOR THE PRODUCTION OF PRODUCTS OF THIS TYPE

CROSS-REFERENCE TO RELATED APPLICATIONS

This application claims priority from and is a continuation of U.S. patent application Ser. No. 12/871,303, filed on Aug. 30, 2010, which claims the benefit under 35 U.S.C. § 119(e) of the filing date of U.S. Provisional Patent Application No. 61/237,866, filed on Aug. 28, 2009, the entirety of which are herein incorporated by reference.

The invention relates to a flavoring mixture comprising one or more sweet-tasting substances as well as phyllodulcin. This flavoring mixture is suitable as an intermediate product for an orally consumable product containing a flavoring mixture of this type, the proportion of conventional sweet-tasting substances in the orally consumable product being reduced. The invention also relates to a process for the production of a reduced-sweetener, orally consumable product and to the use of a corresponding flavoring mixture for the preparation of a product of this type.

Consumers generally have a strong preference for foodstuffs or indulgence foods and also drinks and other orally consumable products which have a high sugar content (particularly sucrose=(saccharose), lactose, glucose or fructose or mixtures thereof) due to the sweetness thereof. On the other hand, it is generally known that a high content of readily metabolizable carbohydrates causes a steep rise in blood sugar levels, leads to the formation of fat deposits and ultimately can result in health problems such as overweight, obesity, insulin resistance, age-onset diabetes and complications thereof. Another particular aggravating factor is that many of the above-mentioned carbohydrates can also have an adverse effect on dental health, as they are decomposed by specific types of bacteria in the oral cavity into lactic acid, for example and can attack the enamel of milk teeth or adult teeth (caries).

Therefore, it has long been an objective to reduce the sugar content of foodstuffs and/or indulgence food and drinks as far as possible, the preferred objective being to achieve this reduction while diminishing the sweetness sensation as little as possible. A suitable measure is to use sweeteners: these are chemically uniform substances which themselves have no, or only a very low calorific value, while at the same time providing a marked sweet taste sensation; in general, the substances are non-cariogenic (a review can be found, for example in Journal of the American Dietetic Association 2004, 104 (2), 255-275). Due to their low application concentration, non-nutritive, high-intensity sweeteners are indeed very suitable for introducing sweetness into foodstuffs, however they often exhibit problems in respect of taste due to dissimilar time-intensity profiles compared to sugar (for example sucralose, *Stevia* products, rebaudiosides, steviosides, cyclamate), a bitter and/or astringent aftertaste (for example Acesulfame-K, saccharin, *Stevia* products, rebaudiosides, steviosides), pronounced additional flavor sensations (for example glycerrhyzic acid ammonium salt). Some of the sweeteners are not particularly heat-stable (for example thaumatin, brazzein, monellin), are not stable in every application (for example aspartame) and some have a very long-lasting sweet effect (strong sweet aftertaste, for example saccharin, *Stevia* products, rebaudiosides, steviosides).

Another possibility—without using non-nutritive sweeteners—is to reduce the sugar content of foodstuffs and/or indulgence foods and to add substances which are sensorially faintly detectable or undetectable and which indirectly or directly enhance the sweetness, as described, for example in WO 2005/041684. However, the substances described in WO 2005/041684 are explicitly of a non-natural origin and thus, from a toxicological point of view, are more difficult to assess than substances of a natural origin, particularly if the latter occur in foodstuffs or indulgence foods or originate from raw materials for the production of foodstuffs or indulgence foods. EP 1 291 342 describes such substances of a natural origin (pyridinium betaines); however, these substances do not influence the sweet taste selectively, but also influence other taste flavors such as umami or saltiness. Furthermore, the disclosed substances can only be purified with great effort.

WO 2007/014879 A1 recommends the use of hesperetin to enhance the sweet taste of reduced-sugar preparations used for nutrition or enjoyment. However, an occasional disadvantage when using hesperetin is its low solubility, particularly in clear, aqueous applications (for example clear cola or still lemonade) and the relatively indistinct sweetness enhancement in acidic foodstuffs and indulgence foods. WO 2007/014879 A1 discloses the use of hesperetin when also combined with 4-hydroxydihydrochalcones. In this respect, it is possible to achieve significant reductions in the quantities of sugar or sweetener with the same sweetness and a substantially adequate solubility, but in many cases it is not possible to reproduce the sweetness with more than a 25% reduction of the sugar and sweetener quantities particularly in strongly acidic (pH<5) applications.

The isocoumarin phyllodulcin which occurs in *Hydrangea dulcis* leaves has already been described as a sweetener (Kinghorn, A. D. and C. M. Compadre (2001). "Less common high-potency sweeteners." Food Sci. Technol. (N.Y.) 112 (Alternative Sweeteners): 209-233, Crosby, G. A. (1976). "New Sweeteners." Critical Reviews in Food Science and Nutrition (June): 297-323). However, the use as a synergistically effective flavoring in particular under the actually only sweet-tasting effect has not been described before.

In fact, JP 11253128 does describe a synergistic combination of *Euonymus* tricocarpus with *Hydrangea dulcis* extracts. However, it emerges from the text that the antioxidative action is the primary effect.

In WO 2005/020721, a drink with a combination of a sweetener, monatin, with phyllodulcin as isolated sweetener is claimed. However, in this case the concentration of phyllodulcin is sufficient to produce a sweet taste even on its own.

WO 2007/121604 describes a process for the identification of modulators of the T1R2-TMD and/or CFR:T1R receptors. Phyllodulcin is also stated in a long list of potential test candidates. However, the document does not give sufficient indication that phyllodulcin could be an enhancer of the receptor systems to be tested, as this compound is merely described as a potential modulator. In particular, the document contains no indication that phyllodulcin could have a synergistically enhancing effect on the sweetness perception in vivo. The mentioned document does not even suggest in which ratios phyllodulcin and sweeteners which may be enhanced should be used in vitro or in vivo.

Against the background of the prior art, the object of the invention was to provide orally-consumable, sweet-tasting products which have a reduced amount of sugar and/or sweetener compared to products with a comparable sweetness sensation. Part of this object was to provide corresponding pre-products or intermediate products in the form of flavoring mixtures which can be used in the orally consumable sweet-tasting products in dilute form and which guarantee the desired effect. The products or flavoring compositions should preferably be stable in respect of the sweetness sensation they impart, the sweetness sensation should be based on naturally occurring compounds and/or the reduction of the quantity of sugar or sweetener should be possible while the sweetness sensation remains the same, without the usual flavoring profile being adversely affected. It was further desired that the agents that allow a reduction in the quantity of sugar or sweetener should be effectively and clearly soluble in water.

This object is achieved in respect of the pre-product or the flavoring mixture by a flavoring mixture comprising (i) one or more sweet-tasting substances, selected from the group of naturally occurring sweet-tasting substances and the physiologically compatible salts thereof without phyllodulcin and the physiologically compatible salts thereof, and (ii) phyllodulcin and/or one or more of the physiologically compatible salts thereof, wherein the ratio of the sucrose equivalence of the concentration of the substance or substances of group (i) to the sucrose equivalence of the concentration of the substance or substances of group (i) is ≥2, preferably ≥3, more preferably ≥4 and particularly preferably ≥6.

The sweet-tasting substance or substances (substances of group (i)) are preferably selected from the group consisting of a) carbohydrates, preferably selected from the subgroup consisting of sucrose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-gyceraldehyde and maltodextrin;

b) naturally occurring sugar alcohols selected from the subgroup consisting of glycerol, erythritol, threitol, arabitol, ribitol, xylitol, sorbitol, mannitol, maltitol, isomaltitol, dulcitol, and lactitol. The carbohydrates can also be present in the form of plant preparations containing one or more of the mentioned carbohydrates, preferably in a proportion of at least 5% by weight, preferably at least 15% by weight). The carbohydrates can also be present as a naturally occurring or artificially produced mixture (for example from honey, invert sugar, syrup, high fructose corn syrup);

c) naturally occurring sweeteners, selected from the subgroup consisting of miraculin, curculin, monellin, mabinlin, thaumatin, curculin, brazzein, pentadin, D-phenylalanine and D-tryptophan;

d) naturally occurring sweeteners, selected from the subgroup consisting of stevioside, steviolbioside, rebaudioside A, further stevilglycosides such as rebaudioside B, rebaudioside C, rebaudioside D, rebaudioside E, rebaudioside F, rebaudioside G, rebaudioside H, dulcoside and/or rubusoside, oslandin, polypodoside A, strogin 1, strogin, 2 strogin 4, selligueanin A, dihydroquercetin-3-acetate, perillartin, telosmoside $A_{15}$, periandrin I-V, pterocaryosides, cyclocaryosides, mukroziosides, trans-anethol, trans-cinnamaldehyde, bryosides, bryonosides, bryonodulcosides, carnosiflosides, scandenosides, gypenosides, trilobatin, phloridzin, dihydroflavanols, hematoxylin, cyanin, chlorogenic acid, albiziasaponin, telosmosides, gaudichaudioside, mogrosides, hernandulcin, glycyrrhetinic acid;

e) the physiologically compatible, sweet-tasting derivatives of the members of subgroups a) to d); and f) the physiologically compatible salts of the members of subgroups a) to e), in particular the potassium, sodium, calcium or ammonium salts thereof.

The sweeteners mentioned in subgroup d) can preferably be present in the form of extracts or fractions which are obtained from natural sources and contain the sweet-tasting amino acids and/or proteins.

Naturally occurring sweeteners in the context of the invention are non-nutritive or only slightly nutritive, in particular sweet-tasting compounds or particularly sweet-tasting natural extracts or isolates and these natural extracts or isolates do not comprise the sweet-tasting carbohydrates, in particular sugar or sugar alcohols in a quantity sufficient for releasing a perceptible sweet taste in the preparation. In this respect, within the context of the invention, the sweeteners must be capable on their own of producing a sweetening potency in the preparation to be consumed (foodstuff, indulgence food) which would correspond to the sweetening potency of an at least 4% aqueous sucrose solution.

The naturally occurring sweeteners from group (i) can also be used in the flavoring mixtures according to the invention in the form of extracts or concentrated fractions of these extracts, in particular Thaumatococcus extracts (Katemfe bush), extracts of *Stevia* ssp. (in particular *Stevia rebaudiana*), Swingle extract (*Momordica* or *Siratia grosvenorii*, luo-han-guo), extracts of licorice root, also *Glycerrhyzia* ssp. (in particular *Glycerrhyzia glabra*), *Rubus* ssp. (in particular *Rubus suavissimus*), citrus extracts, extracts of *Lippia dulcis*, correspondingly concentrated fractions of these extracts.

The sucrose equivalence ratio of the sucrose equivalence of the concentration of the substances or substance of group (i) to the sucrose equivalence of the concentration of the substance or substances of group (ii) in the corresponding flavoring mixture (and in other mixtures, cf. further below), is established as follows:

1. A comparative series of different sucrose concentrations in water is produced. Preferred concentrations are 0; 0.25; 0.5; 0.75; 1; 1.5; 2; 3; 4 and 5% by weight sucrose in water. Other concentrations, in particular higher concentrations, can optionally also be used for the comparative series.
2. An aqueous solution of the sweet-tasting substances of group (i) is produced with an identical concentration of these substances as in the sample to be investigated (solution 1).
3. An aqueous solution of the substances of group (ii) is produced with the same concentration as that of the substances of group (ii) in the sample to be investigated (solution 2).
4. A panel of at least 10 people (preferably people experienced in taste tests, of different ages, backgrounds and sex) tests solution 1 compared to the sucrose series and classifies it in order to determine the sucrose equivalence.
5. The determined sucrose equivalence is produced from the average of individual gradings by the individual panelists.
6. The dilution ratio is then determined, using which solution 1 can be set at a sucrose equivalence of 2% by weight sucrose in water. For this purpose, it can be useful to pre-dilute the test sample before step 4. It is of course sensible to have the determined dilution ratio tested once more by the panelists.

7. Solution 2 (containing the compound(s) of group (ii)) is then diluted in the dilution ratio determined under 6.
8. Subsequently, the dilute solution 2 is also tasted and compared to the sucrose test series, graded by the panelists and a corresponding sucrose equivalence value is determined (analogously to points 4. and 5.).
9. The sucrose equivalence of the dilute solution 1 (equivalent to 2% by weight sucrose in water) is put in the ratio to the sucrose equivalence, determined according to step 8, of the dilute solution 2. This produces the sucrose equivalence ratio.

The particular advantage of the flavoring mixture according to the invention is that it can be used particularly effectively as a pre-product (or intermediate product) for orally consumable products. The sucrose equivalence ratio which has been set for the substances of groups (i) and (ii) allows the sweetness sensation to be synergistically enhanced. In this respect, it should be noted that the substances of group (ii) (phyllodulcin and the physiologically compatible salts thereof) have a very strongly pronounced sweetening potency (and thus a high sucrose equivalence) even in extremely low concentrations. This means that in the flavoring mixtures according to the invention, the concentration of the substances of group (i) is consistently higher by a multiple than the concentration of the substances of group (ii).

The sweetness sensation which can be produced by the flavoring mixture according to the invention or by the dilutions thereof is significantly higher than the sweetness sensation (which can be measured, for example by the sucrose equivalence) of the compounds of group (i) and of group (ii) added together. Therefore, a surprising synergistic effect is present. This synergistic effect is surprisingly to be observed both in the range below as well as in the range above the perception threshold of phyllodulcin (cf. also further below).

A flavoring mixture according to the invention, comprising an extract of *Hydrangea dulcis* as the source of the compound or compounds of group (ii) is preferred according to the invention.

In this context, "*Hydrangea dulcis*" includes all *hydrangea* variations which contain phyllodulcin. Preferred *Hydrangea dulcis* variations are *Hydrangea macrophylla* var. *thunbergii*, *Hydrangea macrophylla* var. oamacha and *Hydrangea macrophylla* var. Amagiana and further *hydrangea* species which naturally contain phyllodulcin.

In some cases it can be preferable for the extract which is preferably contained according to the invention not to be an aqueous extract, in other words an extract which was not exclusively produced using water as the extraction agent.

The advantage of using extracts of this type is that, surprisingly, the phyllodulcin is more stable, i.e. it exhibits a slower degeneration even under relatively rigid conditions for the foodstuff range. In this respect, reference is also made to FIG. 1 and Example 2 (cf. further below).

Thus, it was possible to observe in an aqueous solution of an exemplary extract a stability which was three times higher with the same absolute starting concentration of phyllodulcin.

The presence (or the containment) of an extract of *Hydrangea dulcis* (or the preferred *hydrangea* variations) can preferably be demonstrated by the presence of the compound hydrangenol.

Hydrangenol can also be present in the open form as hydrangeic acid.

For clarification purposes, the structures of the significant ingredients of the extract are combined in the following illustration: phyllodulcin (1), (2S)-phyllodulcin (S-1), hydrangenol (2), (2S)-hydrangenol (S-2), E- and Z-hydrangeic acid (E-3, Z-3).

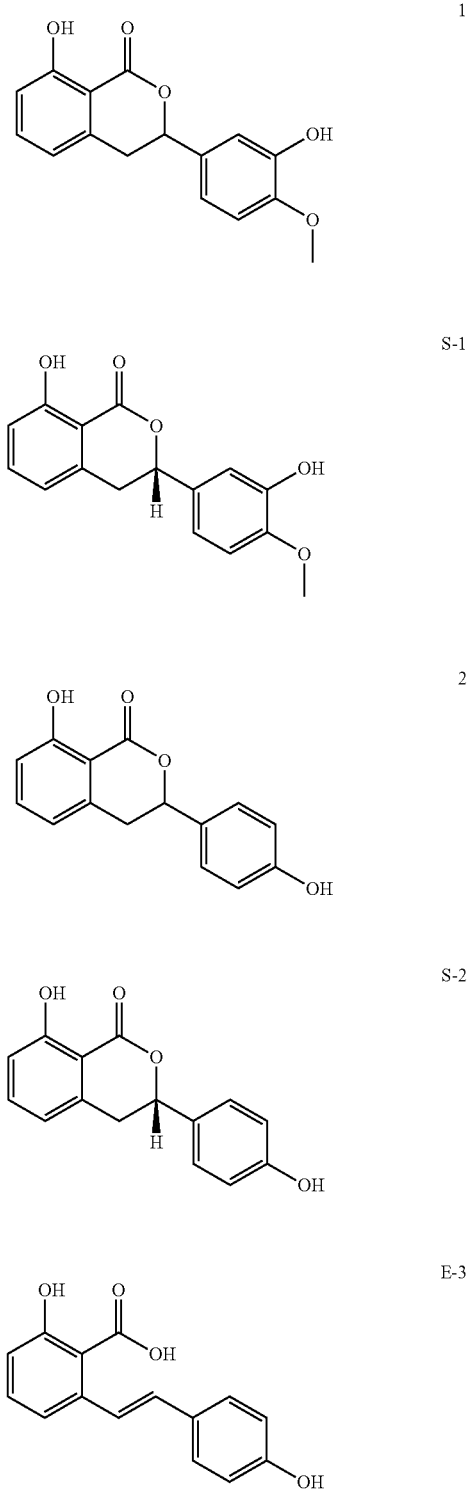

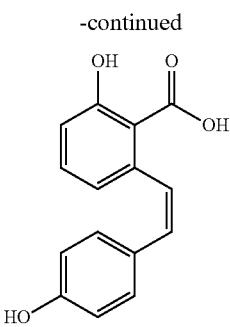

Z-3

For the extract of *Hydrangea dulcis* (in turn preferably *Hydrangea macrophylla* var. *thunbergii*) which is preferably to be used according to the invention, it should preferably contain at least 0.1% by weight and at most 50% by weight, preferably 0.5% by weight to 30% by weight, more preferably 1% by weight to 25% by weight of phyllodulcin and at least 0.01% and at most 50%, preferably 0.01% by weight to at most 30% by weight, more preferably 0.01% by weight to at most 25% by weight of hydrangenol, in each case based on the dry weight of the extract.

The extracts, preferably to be used, for the flavoring mixture preferred according to the invention are preferably obtained by a method in which the leaves of the plant which are dried immediately after harvest
  a) are moistened with water and are fermented, moist, at 10 to 50° C., preferably 15 to 25° C. for 1 to 72 hrs, preferably for 5 to 16 hrs;
  b) the moist, fermented leaves are extracted using a suitable solvent (for example water, subcritical or supercritical water, supercritical $CO_2$, water-ethanol mixtures, ethanol, ethyl acetate, n-heptane, n-hexane, it also being possible for mineral or organic acids such as phosphoric acid, citric acid, malic acid, succinic acid, acetic acid, formic acid, fumaric acid, maleic acid or other permitted food acids to be used) at a temperature of from 0° C. to the boiling point of the respective solvent, under normal pressure, reduced or elevated pressure, for example by the Soxhlet, counter-flow, percolation or simple perforated basket methods (primary extract);
  c) the primary extract is concentrated optionally by distillative or other evaporative or pervaporative processes;
  d) the concentrated primary extract is optionally purified by treating with adsorbing agents (silica gel, activated carbon, kieselguhr, alumina, basic or acidic or neutral ion exchangers) in the batch or column methods (secondary extract);
  e) the secondary extract is dried by evaporative or pervaporative processes;
  f) and optionally the dried secondary extract is taken up again in suitable solvents or mixtures (ethanol, 1,2-propylene glycol, vegetable oil glycerides, triacetin, glycerol); and
  g) is adjusted acidically using mineral or organic acids such as phosphoric acid, citric acid, malic acid, succinic acid, acetic acid, formic acid, fumaric acid, maleic acid or other permitted food acids.

Evaporative or pervaporative processes can be, for example distillation, sublimation, water vapor distillation, freeze-drying, pervaporative membrane processes or spray-drying, and suitable auxiliaries and carriers can also be added for this purpose before this treatment.

The process is carried out such that the extract contains 0.1% by weight and at most 50% by weight, preferably 0.5% by weight to 30% by weight, more preferably 1% by weight to 25% by weight of phyllodulcin and at most 50%, preferably 0.01% by weight to at most 30% by weight, more preferably 0.01% by weight to at most 25% by weight of hydrangenol.

A preferred flavoring mixture according to the invention further comprises one or more substances, selected from group (iii), consisting of flavoring and/or aromatic substances which enhance a sweet taste, and the physiologically compatible salts thereof.

Surprisingly, it has been found that in addition to the synergistic effect of sweetness enhancement produced by phyllodulcin or the salts thereof, a further synergistic effect is produced using further sweetness enhancers known from the prior art.

The following are particularly preferred as further sweetness enhancers in this connection:
  Hesperetin according to WO 2007/014879 A1
  Hydroxyphenylalkadiones according to WO 2007/003527 A1
  4-hydroxychalkones according to WO 2007/107596 A1 and EP 1 972 203
  Propenylphenylglycosides (chavicol glycosides) according to EP 1 955 601 A1
  Divanillins and/or
  Hydroxyflavans.

The products according to the invention can contain according to group (iii) one or more divanillins, in particular those as described in WO 2004/078302, while 6,6'-dihydroxy-5,5'-dimethoxy-biphenyl-3,3'-dicarbaldehyde is preferred.

The products according to the invention can contain one or more naturally occurring 4-hydroxydihydrochalcones according to group (iii), in particular those as described in WO 2007/107596 and EP 1 972 203. 3-(4-hydroxyphenyl)-1-(2,4-dihydroxyphenyl)propan-1-one (davidigenin) and/or 3-(4-hydroxyphenyl)-1-(2,4,6-trihydroxyphenyl)propan-1-one (phloretin) in particular are preferred.

Hesperetin in the context of an ingredient according to group (iii) of a flavoring mixture according to the invention can be in particular the (2S)-enantiomer, the (2R)-enantiomer or a mixture of these enantiomers, as described in particular in WO 2007/014879.

A flavoring mixture according to the invention can preferably be contained according to group (iii) as propenylphenyl glycoside (chavicol glycoside), the alpha- or beta-anomers and most particularly the beta-anomers of 1-0-[4-(propen-2-enyl)phenyl]-D-glucopyranoside (chavicol glucoside), 1-0-[4-(propen-2-enyl)phenyl]-6-0-ß-D apiofuranosyl-D-glucopyranoside (furcatin), 1-0-[4-(Propen-2-enyl)phenyl]-6-0-ß-D-rutinoside and/or of 1-0-[4-(propen-2-enyl)phenyl]-O-ß-D-xylopyranosyl-(1-6)-ß-D-glucopyranoside (p-allylphenylprimeveroside, miyaginin).

Isogingerdione-2 is preferred as hydroxyphenylalkane dione.

3',7-dihydroxy-4'-methoxyflavan and/or (S)-3',7-dihydroxy-4'-methoxyflavan is preferred as hydroxyl flavan.

Within the context of the objects set above, the invention also relates to an orally consumable product, comprising a flavoring mixture according to the invention. In the product according to the invention, the ratio of the sucrose equivalence of the concentration of the substance or substances of group (i) to the sucrose equivalence of the concentration of the substance or substances of group (ii) is ≥2, preferably ≥3, more preferably ≥4 and particularly preferably ≥6. Within this range, the synergistic enhancing effect of phyllodulcin can be utilized particularly effectively, such that the orally consumable product is ultimately obtained with a significantly reduced use of concentrations of compounds of group (i), while the sweetness remains the same.

Of course, the orally consumable product according to the invention optionally comprises one or more further conventional foodstuff ingredients.

The concentration of the flavoring mixture in the orally consumable product is preferably set such that the concentration of the substances of group (ii) is from 0.5 to 15 ppm, based on the weight of the product.

The synergistic effect of phyllodulcin and the salts thereof in respect of the sweetness enhancement can be utilized even in this low concentration. This is surprising in view of the prior art. Furthermore, the use of such reduced concentrations of phyllodulcin in the orally consumable product (and of course particularly in the end product) had the advantage that unpleasant secondary flavoring notes of phyllodulcin are not detected or are only detected without being disturbing. Thus, phyllodulcin has already been described as a sweetener (Crosby, G. A. (1976). "New Sweeteners." *Critical Reviews in Food Science and Nutrition* (June): 297-323). However, this document described the strong secondary taste and also an aftertaste as serious disadvantages. The result of this was that in spite of the significant sweetening effect of phyllodulcin, hitherto it has not been routinely used as a sweetener.

An orally consumable product according to the invention is preferred in which the concentration of the flavoring mixture is adjusted such that the concentration of the substances of group (i) alone has a sucrose equivalence of a solution of ≥4% by weight, preferably ≥6% by weight of sucrose in water.

Surprisingly, the synergistic enhancing effect of the sweetening action released by phyllodulcin or the salts thereof can be achieved particularly well in orally consumable products in which the concentration of the substances of group (i) is adjusted such that it has a sucrose equivalence of more than or equal to 4% by weight, preferably more than or equal to 6% by weight of sucrose in water.

In the orally consumable products according to the invention, the upper limit for phyllodulcin is preferably 15 ppm, more preferably 10 ppm, more preferably 5 ppm and, if it is present, the upper limit for hydrangenol is 50 ppm, the preferred lower limit for hydrangenol being 0.01 ppm, in each case based on the total weight of the orally consumable product.

According to the invention, it is further preferred that if an extract of *Hydrangea dulcis* is contained in the product according to the invention, this extract also contributes to the complete flavoring of the product with a non-sweet flavoring note.

Preferred according to the invention is a flavoring mixture of the invention in which the substance or substances of group (iii) is/are selected from the group consisting of:
 hesperetin
 phloretin
 3',7-dihydroxy-4'-methoxyflavan and
 (S)-3',7-dihydroxy-4'-methoxyflavan.

Furthermore, a flavoring mixture according to the invention is preferred which contains one or more further flavorings, auxiliaries and/or carriers.

In addition, it is preferred that phyllodulcin is present in the flavoring mixtures according to the invention, being concentrated in the S form (cf. formula S-1). The enantiomer excess is preferably between 1 and 100%.

Most particularly preferred according to the invention is an orally consumable sweet-tasting product, comprising
(i) one or more naturally occurring sweet-tasting substances including the physiologically compatible salts thereof, preferably selected from the group consisting of:
 a) carbohydrates (sugars), selected from the subgroup consisting of sucrose, D-fructose, D-glucose and plant preparations containing one or more of the mentioned carbohydrates, (preferably in a proportion of at least 5% by weight, preferably at least 15% by weight), and these carbohydrates can also be present as a natural or synthetically produced mixture (for example as honey, invert sugar syrup, high fructose corn syrup);
 b) sugar alcohols selected from the subgroup consisting of glycerol and erythritol,
 d) sweeteners selected from the subgroup consisting of stevioside, rebaudioside A and rubusoside, and extracts or concentrated fractions of these extracts can also be used, for example *Stevia* extracts and *Rubus suavissimus* extracts,
 alone or in mixtures
 provided that the sweetness of the mentioned sweet-tasting substances of group (i) jointly in the orally consumable sweet-tasting product according to the invention is sensorially equivalent to an at least 6% aqueous sucrose solution,
and
ii) an extract of *Hydrangea macrophylla* var. *thunbergii* (Makino), comprising phyllodulcin and hydrangenol in a concentration such that, based on the orally consumable sweet-tasting product, at least 0.00005% by weight (0.5 ppm) and at most 0.0015% by weight (15 ppm) of phyllodulcin and at least 0.000001% by weight and at most 0.0050% by weight of hydrangenol are contained, the extract also having a non-sweet flavoring and taste characteristic
and
(iii) one or more sweetness-enhancing flavoring and/or aromatic substances including the physiologically compatible salts thereof, in each case selected from the group consisting of
 hesperetin
 phloretin
 3',7-dihydroxy-4'-methoxyflavan or (S)-3',7-dihydroxy-4'-methoxyflavan
and optionally
(iv) one or more further conventional foodstuff ingredients, flavorings, auxiliaries or carriers.

As mentioned, in the orally consumable, sweet-tasting products according to the invention, the concentrations of the compounds of group (i) are preferably overall sensorially equivalent to a ≥4% by weight, preferably 6% by weight aqueous sucrose solution. However, in this respect the ratio of the naturally occurring sweet-tasting substances of group (i) among one another can be freely selected. In this case, the compounds of groups (i) a) and/or (i) b) are preferably used in a concentration sensorially equivalent to an at least 3%, preferably 5% by weight aqueous sucrose solution and the compounds of groups (i) c) and/or (i) d) are preferably used in a concentration sensorially equivalent to an most 2% by weight, preferably at most 1% by weight aqueous sucrose solution. A reduction in sugar can be achieved particularly effectively in this manner, without any impairment to the taste sensation.

Surprisingly, it has been found that in the orally consumable, sweet-tasting products according to the invention, the sweetness is enhanced to a substantially greater extent (not additively, but synergistically, cf. above as well and Examples) than in comparative products which do not contain this combination according to the invention. In particular, the use of the extract in the form and concentration described above is advantageous due to the flavoring characteristics which are present and which round off the sweetness profile of the orally consumable, sweet-tasting products according to the invention, making it more similar to sugar and more stable.

An orally consumable product according to the invention is preferred which is selected from the group consisting of a pharmaceutical preparation, an oral care preparation, a semi-finished product and a liquid or solid foodstuff.

The orally consumable product is more preferably a sweet-tasting drink which can also be carbonized, and comprises
(i) one or more naturally occurring sweet-tasting substances including the physiologically compatible salts thereof, preferably selected from the group consisting of:
  a) carbohydrates (sugars), selected from the subgroup consisting of sucrose, D-fructose, D-glucose and high fructose corn syrup
  d sweeteners selected from the subgroup consisting of stevioside, rebaudioside A and rubusoside, and extracts or concentrated fractions of these extracts can also be used, for example Stevia extracts and Rubus suavissimus extracts,
  alone or in mixtures
  provided that firstly at least one sweet-tasting substance is selected in each case from groups a) and d)
  and
  that the sweetness of the mentioned sweet-tasting substances in the mixture in the orally consumable, sweet-tasting product according to the invention is sensorially equivalent to an at least 6% aqueous sucrose solution
  and
  preferably further provided that the total of the concentration of the compounds of groups (i) a) and/or (i) b) is sensorially equivalent to an at least 5% aqueous sucrose solution and that of group (i) d) is sensorially equivalent to an at least 1% aqueous sucrose solution,
and
(ii) an extract of *Hydrangea macrophylla* var. *thunbergii* (Makino), comprising phyllodulcin and hydrangenol in a concentration such that, based on the orally consumable sweet-tasting product, at least 0.00005% by weight (0.5 ppm) and at most 0.0015% by weight (15 ppm) of phyllodulcin and at least 0.000001% by weight and at most 0.0050% by weight of hydrangenol are contained, the extract also having a non-sweet flavoring and taste characteristic,
and
(iii) one or more sweetness-enhancing flavoring and/or aromatic substances including the physiologically compatible salts thereof, selected from the group consisting of
  hesperetin
  phloretin
  3',7-dihydroxy-4'-methoxyflavan and
  (S)-3',7-dihydroxy-4'-methoxylavan
and optionally
(iv) one or more further flavorings, auxiliaries or carriers.

(Carbonized) sweet-tasting drinks which are preferred according to the invention include carbonized, acid-containing and fruit-containing soft drinks (for example orange, lime or lemon-type soft drinks), carbonized isotonic drinks (for example orange, lime or lemon types), carbonized acidic soft drinks (for example cola, lemon, orange, lime, cherry, apple, vanilla-types or a mixture thereof), carbonized spritzers, carbonized fruit and vegetable juices, carbonized fruit or vegetable juice preparations.

"Carbonized" within the context of the invention means that the drink contains naturally introduced carbon dioxide (for example from fermentation processes as in beer production or by water from carbon dioxide-containing mineral sources) or that carbon dioxide is added to the drink during the production and/or bottling processes.

Preferred auxiliaries or carriers include maltodextrin, starch, natural or artificial polysaccharides and/or vegetable gums such as modified starches or gum arabic, solvents permitted for the flavoring mixtures, for example ethanol, 1,2-propylene glycol, water, glycerol, triacetin, vegetable oil triglycerides, coloring agents, for example permitted foodstuff dyes, coloring plant extracts, stabilizers, preservatives, antioxidants and viscosity-influencing substances.

An orally consumable sweet-tasting product which is preferred according to the invention contains the components of the following groups in the following quantities:
(i a) from 1 to 90% by weight, preferably from 5 to 30% by weight,
(i b) from 1 to 90% by weight, preferably from 1 to 20% by weight,
(i c) from 0.001 to 1% by weight, preferably from 0.01 to 0.5% by weight,
(i d) from 0.0001 to 0.5% by weight, preferably from 0.0001 to 0.1% by weight;
(ii) at least 0.5 ppm and at most 15 ppm of phyllodulcin and at least 0.000001 by weight and at most 0.0050% by weight of hydrangenol;
(iii) from 0.0001 to 0.1% by weight, preferably 0.0005 to 0.05% by weight; and
(iv) from 0 to 99% by weight, preferably from 10 to 95% by weight
in each case based on the weight of the total, orally consumable sweet-tasting product.

As already stated, orally consumable products preferred according to the invention as well as flavoring mixtures preferred according to the invention comprise further flavorings.

Preferred flavorings are flavorings which give rise to a sweet taste sensation, the further flavoring or flavorings which give rise to a sweet taste sensation preferably being selected from the group consisting of:
vanillin, ethyl vanillin, ethyl vanillin isobutyrate (=3-ethoxy-4-isobutyryloxybenz-aldehyde), Furaneol® (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3 (2H)-furanone and 5-ethyl-2-methyl-4-hydroxy-3(2H)-furanone), maltol and derivatives (e.g. ethylmaltol), coumarin and derivatives, gamma-lactones (e.g. gamma-undecalactone, gamma-nonalactone), delta-lactones (e.g. 4-methyldeltalactone, massoilactone, deltadecalactone, tuberolactone), methyl sorbate, divanillin, 4-hydroxy-2(or 5)-ethyl-5(or 2)-methyl-3(2H)furanone 2-hydroxy-3-methyl-2-cyclopentenones, 3-hydroxy-4,5-dimethyl-2(5H)-furanone, fruit esters and fruit lactones (e.g. acetic acid-n-butyl ester, acetic acid isoamyl ester, propionic acid ethyl ester, butyric acid ethyl ester, butyric acid-n-butyl ester, butyric acid isoamyl ester, 3-methyl-butyric acid ethyl ester, n-hexanoic acid ethyl ester, n-hexanoic acid allyl ester, n-hexanoic acid-n-butyl ester, n-octanoic acid ethyl ester, ethyl-3-methyl-3-phenylglycidate, ethyl-2-trans-4-cis-decadienoate), 4-(p-hydroxyphenyl)-2-buta none, 1,1-di methoxy-2,2,5-trimethyl-4-hexane, 2,6-dimethyl-5-hepten-1-al, 4-hydroxycinnamic acid, 4-methoxy-3-hydroxycinnamic acid, 3-methoxy-4-hydroxycinnamic acid, 2-hydroxycinnamic acid, 2,4-dihydroxybenzoic acid, 3-hydroxybenzoic acid, 3,4-dihydroxybenzoic acid, vanillic acid, homovanillic acid, vanillomandelic acid and phenylacetaldehyde.

A flavoring mixture which is particularly preferred according to the invention or an orally consumable product according to the invention also comprises at least one flavoring for enhancing a salty, optionally slightly acidic and/or umami taste sensation. Thus, the flavoring mixtures and products according to the invention are used in combination with at least one (further) substance suitable for enhancing a pleasant taste sensation (salty, umami, optionally slightly acidic). In this respect, salty-tasting compounds and salt-enhancing compounds are preferred. Preferred compounds are disclosed in WO 2007/045566. Umami compounds which are described in WO 2008/046895 and EP 1 989 944 are also preferred.

Furthermore, flavoring mixtures and products preferred according to the invention can also comprise flavorings for masking bitter and/or astringent taste sensations (taste correctors). The (further) taste correctors are selected, for example from the following list: nucleotides (for example adenosine-5'-monophosphate, cytidine-5'-monophosphate) or the pharmaceutically acceptable salts thereof, lactisoles, sodium salts (for example sodium chloride, sodium lactate, sodium citrate, sodium acetate, sodium gluconoate), further hydroxyflavanones, (for example eriodictyol, homoeriodictyol or the sodium salts thereof), in particular according to US 2002/0188019, hydroxybenzoic acid amides according to DE 10 2004 041 496 (for example 2,4-dihydroxybenzoic acid vanillylamide, 2,4-d ihydroxybenzoic acid-N-(4-hydroxy-3-methoxybenzyl)amide, 2,4,6-trihydroxybenzoic acid-N-(4-hydroxy-3-methoxybenzyl)amide, 2-hydroxybenzoic acid-N-4-(hydroxy-3-methoxybenzyl)amide, 4-hydroxybenzoic acid-N-(4-hydroxy-3-methoxybenzyl)amide, 2,4-d ihydroxybenzoic acid-N-(4-hydroxy-3-methoxybenzyl)amide-mono-sodium salt, 2,4-dihydroxybenzoic acid-N-2-(4-hydroxy-3-methoxyphenyl)ethylamide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), bitter-masking hydroxydeoxybenzoins, for example according to WO 2006/106023 (for example 2-(4-hydroxy-3-methoxyphenyl)-1-(2,4,6-trihydroxyphenyl) ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone)), amino acids (for example gamma-butyric acid according to WO 2005/096841 for reducing or masking an unpleasant taste sensation such as bitterness), malic acid glycosides according to WO 2006/003107, salty-tasting mixtures according to PCT/EP 2006/067120, diacetyl trimers according to WO 2006/058893, mixtures of whey proteins with lecithins and/or bitter-masking substances such as gingerdiones according to WO 2007/003527.

The orally consumable sweet-tasting products in the context of the invention are, for example bakery products (for example bread, dry biscuits, cakes and other cookies), confectionery (for example chocolate, chocolate bar products, other products in bar form, fruit gums, hard and soft caramels and chewing gum), alcoholic or non-alcoholic drinks (for example coffee, tea, iced tea, wine, drinks containing wine, beer, drinks containing beer, liqueurs, schnapps, brandies, (carbonized) sodas containing fruit, (carbonized) isotonic drinks, (carbonized) soft drinks, high juice drinks, spritzers, fruit and vegetable juices and fruit or vegetable preparations, instant drinks (for example instant cocoa drinks, instant tea drinks, instant coffee drinks, instant fruit drinks), meat products (for example ham, fresh or raw sausage preparations, seasoned or marinated fresh or salt meat products), eggs or egg products (dried egg, egg white and egg yolk), cereal products (for example breakfast cereals, muesli bars and precooked finished rice products), milk products (for example milk drinks, buttermilk drinks, ice milk, yogurt, kefir, cream cheese, soft cheese, hard cheese, powdered milk, whey, whey drinks, butter, buttermilk, partially or fully hydrolyzed milk protein-containing products), products from soya protein or other soybean fractions (for example soya milk and products produced therefrom, fruit drinks with soya protein, soya lecithin-containing preparations, fermented products such as tofu or tempeh or products produced therefrom), products from other vegetable protein sources, for example oat protein drinks, fruit preparations (for example jams, sorbets, fruit sauces and fruit fillings), vegetable preparations (for example ketchup, sauces, dried vegetables, deep-frozen vegetables, precooked vegetables and preserved vegetables), snack foods (for example baked or fried potato chips or potato dough products and corn or peanut-based extrudates), fat and oil-based products or emulsions thereof (for example mayonnaise, remoulade, dressings), other ready meals and soups (for example powdered soups, instant soups, precooked soups), spices, seasoning mixtures and in particular seasonings which are used, for example in the snacks sector.

The orally consumable, sweet-tasting products in the context of the invention can also be used as semi-finished products in the production of further orally consumable, sweet-tasting products. The orally consumable, sweet-tasting products in the context of the invention can also be present in the form of capsules, tablets (uncoated and coated tablets, for example with an enteric coating), sugar-coated pills, granules, pellets, solids mixtures, dispersions in liquid phases, as emulsions, powders, solutions, pastes or as other preparations which can be swallowed or chewed as food supplements.

Orally consumable, sweet-tasting products in the context of the invention which are particularly preferred are alcoholic drinks, such as mixed beer drinks, mixed wine drinks or other mixed drinks containing at most 5% by volume of alcohol and/or non-alcoholic drinks such as tea, iced tea (sweetened, for example also with herb flavorings or lemon or orange-type fruit flavorings), (carbonized) fruit-containing soft drinks (for example orange, lime or lemon types), (carbonized) isotonic drinks (for example orange, lime or lemon types), (carbonized) soft drinks (for example cola, lemon, orange, lime, cherry, apple, vanilla types or a mixture thereof), high juice drinks, spritzers, milk drinks, buttermilk drinks, yoghurt, kefir, whey drinks, soya milk and products produced therefrom, fruit drinks with soya protein, oat protein drinks and instant drinks (for example instant cocoa drinks, instant tea drinks, instant coffee drinks, instant fruit drinks), so-called flavored waters ("near-water" drinks, it being necessary for the latter to be sweetened.

"Near-water" drinks in this context are (carbonized) drinks based on (mineral) water which are for the most part clear, are only faintly colored, are often only slightly sweetened (less than 5% sucrose or sweeteners with a sweetening potency of less than 5% sucrose), are mostly not acidified or only slightly acidified and have a pH range of approximately 4 to 8, are mostly only flavored and can be provided with minerals, vitamins and/or plant extracts. In contrast to most other drinks (for example soft drinks, fruit juice drinks, [iced] tea drinks, etc.), the "water" nature of the drink is still always significant.

Drinks are preferred which have a pH value of less than 7, more preferably less than 5 and in particular preferably less than 4.

Orally consumable, sweet-tasting products according to the invention can also be oral care or pharmaceutical preparations.

Oral care preparations within the present context include in particular oral and/or dental care products, such as toothpastes, dental gels, dental powders, mouthwash, chewing gum and other oral care products.

Pharmaceutical preparations comprise a pharmaceutical active ingredient. Advantageous pharmaceutical active ingredients include, for example steroidal anti-inflammatory substances of the corticosteroid type, such as hydrocortisone, hydrocortisone derivatives such as hydrocortisone-17-butyrate, dexamethasone, dexamethasone phosphate, methylprednisolone or cortisone.

Advantageous non-steroidal pharmaceutical active ingredients include, for example anti-inflammatory agents such as oxicams, for example piroxicam or tenoxicam; salicylates such as Aspirin® (acetylsalicylic acid), disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, flurbiprofen, benoxaprofen or pyrazoles, such as phenyl butazone, oxyphenylbutazone, febrazone or azapropazone.

Pharmaceutical preparations which are particularly preferred are non-prescription-only products and so-called "over the counter" (OTC) preparations, containing active ingredients such as paracetamol, acetylsalicylic acid or ibuprofen, vitamins (for example vitamin H, vitamins from the B series such as vitamin B1, B2, B6, B12, niacin, panthotenic acid, preferably in the form of (effervescent) tablets or capsules), minerals (preferably in the form of (effervescent) tablets or capsules), such as iron salts, zinc salts, selenium salts, products containing active ingredients or extracts of ribwort (for example in cough syrup) or St. John's wort.

Further conventional foodstuff ingredients can be active ingredients, basic substances, auxiliaries and additives. Further conventional active ingredients, basic substances, auxiliaries and additives for orally consumable, sweet-tasting products can be contained in quantities of from 5 to 99.999999% by weight, preferably from 10 to 80% by weight, based on the total weight of the preparation. Furthermore, the orally consumable, sweet-tasting products can contain water in a quantity of up to 99.999999% by weight, preferably from 5 to 80% by weight, based on the total weight of the preparation.

The invention also relates to a process for the preparation of a sweetener-reduced, orally consumable product, comprising the following steps:
a) preparation of a flavoring mixture or of the individual ingredients of such a flavoring mixture, and
b) incorporation of the flavoring mixture or ingredients of the flavoring mixture prepared in step a) into an orally consumable product, such that the ratio of the sucrose equivalence of the concentration of the substance or substances of group (i) to the sucrose equivalence of the concentration of the substance or substances of group (ii) in the ready prepared orally consumable product is ≥2, preferably ≥3, more preferably ≥4 and particularly preferably ≥6.

In this respect, a process according to the invention is preferred in which step b) is carried out such that in the ready prepared orally consumable product, the concentration of the substances of group (ii) is from 0.5 to 15 ppm, based on the weight of the product and/or the concentration of the substances of group (i) alone has a sucrose equivalence of a solution of ≥4% by weight, preferably ≥6% by weight of sucrose in water.

According to a preferred embodiment, the products according to the invention are prepared in that the ingredients of groups (i), (ii) and optionally also (iii) of the flavoring mixture according to the invention are incorporated into a base preparation used for nutrition, oral care or enjoyment or an oral pharmaceutical base preparation as substances, as a solution or in the form of a mixture with a solid or liquid carrier. Preparations according to the invention which are present as a solution can advantageously also be transformed into a solid preparation by spray-drying.

According to a further preferred embodiment, for the preparation of orally consumable products according to the invention, flavoring mixtures according to the invention in the form of emulsions are incorporated into liposomes, for example starting from phosphatidyl choline, into microspheres, nanospheres or also into capsules, granules or extruded material from a matrix suitable for foodstuffs and indulgence foods, for example from starch, starch derivatives, cellulose or cellulose derivatives (for example hydroxypropyl cellulose), other polysaccharides (for example alginate), natural fats, natural waxes (for example beeswax, carnauba wax) or from proteins, for example gelatin.

In a further preferred production process, the flavoring mixture according to the invention is complexed with one or more suitable complex formers, for example with cycloglycanes, for example cyclofructanes, cyclodextrins or cyclodextrin derivatives, preferably α-, γ- and β-cyclodextrin, and are used in this complexed form.

An orally consumable, sweet-tasting product according to the invention is particularly preferred in which the matrix is selected such that the flavoring mixture according to the invention is released in a delayed manner from the matrix, thereby providing a long-lasting effect.

Conventional basic substances, auxiliaries and additives for foodstuffs or indulgence foods can be used as further ingredients for orally consumable, sweet-tasting products according to the invention.

Examples of conventional basic substances, auxiliaries and additives include water, mixtures of fresh or processed, animal or vegetable basic substances or raw materials (for example raw, roast, dried, fermented, smoked and/or boiled meat, bone, cartilage, fish, vegetables, fruits, herbs, nuts, vegetable or fruit juices or pastes or mixtures thereof), digestible or indigestible carbohydrates (for example dextrins, amylose, amylopectin, inulin, xylanes, cellulose), natural or hardened fats (for example tallow, lard, palm oil, coconut butter, hardened vegetable fat), oils (for example sunflower oil, peanut oil, corn oil, olive oil, fish oil, soya bean oil, sesame oil), fatty acids or the salts thereof (for example potassium stearate), proteinogenic or non-proteinogenic amino acids and related compounds (for example taurin), peptides, native or processed proteins (for example gelatin), enzymes (for example peptidases), nucleic acids, nucleotides, other taste correctors than those already described for unpleasant taste sensations, taste correctors for further generally not unpleasant taste sensations, taste-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols), stabilizers (for example carrageenan, alginate), preservatives (for example benzoic acid, sorbic acid), antioxidants (for example tocopherol, ascorbic acid), gelators (for example citric acid), organic or inorganic acidulants (for example malic acid, acetic acid, citric acid, tartaric acid, phosphoric acid), additional bitter principles (for example quinine, caffeine, limonine, amarogentin, humolones, lupolones, catechins, tannins), mineral salts (for example sodium chloride, potassium chloride, magnesium chloride, sodium phosphates), substances preventing enzymatic browning (for example sulfite, ascorbic acid), ethereal oils, plant extracts, natural or synthetic dyes or colored pigments (for example carotenoids, flavonoids, anthocyans, chlorophyll and derivatives thereof), spices, synthetic, natural or nature identical flavoring or aromatic substances as well as odor correctors.

Dental care products (as a base for oral care preparations) which contain the flavoring mixture according to the invention, preferably comprise an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, other taste correctors for unpleasant taste sensations, taste correctors for further normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol, menthol derivatives, (for example L-menthol, L-menthyl lactate, L-menthyl alkyl carbonates, menthone ketals, menthane carboxylic acid amides), 2,2,2-trialkylacetic acid amides (for example 2,2-diisopropylpropionic acid methyl amide), icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings, sodium bicarbonate and/or taste correctors.

Chewing gums (as a further example of oral care preparations) which contain a flavoring mixture according to the invention, preferably comprise a chewing gum base, i.e. a chewable mass which becomes malleable while being chewed, different types of sugar, sugar substitutes, sweeteners, sugar alcohols, other taste correctors for unpleasant taste sensations, taste correctors for further generally not unpleasant taste sensations, taste-modulating substances (for example inositol phosphate, nucleotides such as guanosine monophosphate, adenosine monophosphate or other substances such as sodium glutamate or 2-phenoxypropionic acid), the cooling active ingredients mentioned in the previous section, humectants, thickeners, emulsifiers, flavorings, stabilizers and/or odor correctors.

The orally consumable, sweet-tasting products according to the invention are routinely products which are intended to be introduced into the human oral cavity, to remain there for a certain period of time and then to either be consumed (for example ready-to-eat foodstuff) or removed again from the oral cavity (for example chewing gum or toothpaste). It is understood that the use of the flavoring mixture according to the invention can be provided for any type of such products. Included with these products are all substances or products which are intended to be received in the human oral cavity in a processed, part-processed or unprocessed state. This also includes substances which are added to foodstuffs during the production, processing or treatment thereof and are intended to be introduced into the human oral cavity.

It is understood that the flavoring mixture according to the invention can be used in particular in foodstuffs. In the present context, the term "foodstuff" is understood in particular as meaning substances which are intended to be swallowed by humans in an unaltered state or in a prepared or processed state and then consumed; the term "foodstuff" is also understood as meaning sheathings, coatings or other encapsulations which are intended to also be swallowed, or for which swallowing is to be envisaged. Specific products which are usually removed from the oral cavity (for example chewing gum) are also understood as a foodstuff in the present context, since it cannot be ruled out that at least portions thereof are swallowed.

The flavoring mixture according to the invention is used in particular in ready-to-eat foodstuffs. The term "ready-to-eat foodstuff" is understood in this context as meaning a foodstuff which is already fully constituted in respect of the substances which determine the taste. The term "ready-to-eat foodstuff" also includes corresponding drinks as well as solid or semi-solid ready-to-eat foodstuffs. Examples include deep-frozen products which, before consumption, have to be defrosted and heated to consumption temperature. Products such as yoghurt or ice cream, but also chewing gum or hard caramels are also included as ready-to-eat foodstuffs.

An oral care preparation (also called an oral hygiene product or oral hygiene preparation) in the context of the invention is understood as meaning a preparation for cleaning and caring for the oral cavity and throat and also for freshening breath. This explicitly includes care of the teeth and gums. Application forms of conventional oral hygiene formulations are creams, gels, pastes, foams, emulsions, suspensions, aerosols, sprays as well as capsules, granules, pastilles, tablets, candies or chewing gums, on the understanding that this list is not restrictive for the purposes of this invention.

As already mentioned, the flavoring mixture according to the invention can also be used in semi-finished foodstuff products. The term "semi-finished foodstuff product" relates in this respect to foodstuffs which are intended to be consumed only in a further processed state, for example after the addition of flavorings or aromatic substances which (co)determine the sensory impression.

According to what has been stated above, the invention also relates to the use of a flavoring mixture according to the invention for the production of a reduced-sweetener orally consumable product.

As already described above in depth, this use makes it possible to produce a given taste sensation (sweetness), at the same time with a reduction in the use of sweet-tasting substances according to group (i).

Furthermore, the invention also relates to the use of an extract of *Hydrangea dulcis* for the production of an orally consumable product with a stabilized content of a compound or compounds, selected from group (ii), consisting of phyllodulcin and the physiologically compatible salts thereof, the product comprising one or more sweet-tasting substances, selected from group (i) of naturally occurring sweet-tasting substances and the physiologically compatible salts thereof without phyllodulcin and the physiologically compatible salts thereof.

In this manner, it is possible to provide flavoring mixtures and orally consumable end products in which the proportion of phyllodulcin or the salts thereof is stabilized such that the advantageous effect of these compounds can also be used over a reduced period of time.

In the following, the invention will be further described on the basis of examples and the claims. The examples serve to illustrate the invention, without restricting the scope of protection of the claims. All quantities relate to weight, unless indicated otherwise.

EXAMPLES

Example 1: Consecutive Extraction of *Hydrangea dulcis*

100 g of plant material (mainly leaves) dried directly from/out of the living plant (*Hydrangea dulcis*) are moistened with deionized water and left to stand for 16 hrs at room temperature such that fermentation takes place. The fermented plant material is dried again for 3 hrs at 40° C. 100 g of the fermented, dried plant material is then extracted with stirring using different solvents in increasing polarity (heptane, methylene chloride, ethyl acetate, ethanol/water 4:1) for 1 hour in each case at room temperature. The solvent is removed under vacuum and the dried extracts are tasted in a dose of 500 ppm on sugar solution (5%) and salt solution (0.5%) and assessed sensorially.

| Solvent | Yield | Content of phyllodulcin (based on dry mass) | Sensory assessment |
| --- | --- | --- | --- |
| Heptane | 0.8 g | 12.7% | Herby, sweet, sweetener note |
| Methylene chloride | 1.6 g | 15.4% | Sweetener note, licorice, bitter |
| Ethyl acetate | 1.7 g | 10.5% | Bitter, sweet, green, herby |
| Ethanol/water | 20.2 g | 1.4% | Bitter, sweet, herby |

Example 2: Production of an Ethanolic *Hydrangea dulcis* Dry Extract 2 g of dried fermented plant material (produced as described in Example 1) were extracted in 50 ml of ethanol for one hour under reflux. The solvent was removed under vacuum and the dried extract was tasted in a dose of 110 ppm on sugar solution (5%) and assessed sensorially.

| Solvent | Yield | Content of phyllodulcin (based on dry mass) | Sensory assessment |
| --- | --- | --- | --- |
| Ethanol | 0.29 g | 7.2% | Herby, sweet, licorice, depth, woody |

The exemplary extract was tested for stability under an elevated thermal stress in comparison to pure phyllodulcin. A solution of 100 mg/l of phyllodulcin and 1.38% of the exemplary ethanolic extract (corresponds to 100 mg of phyllodulcin) in an aqueous phosphate buffer, adjusted to pH 9, was tested immediately after preparation and then at regular weekly intervals for its phyllodulcin content. In this respect, an aliquot of the respective test solution was separated in an HPLC installation (RP phase) and quantified by UV detection compared to a calibration with pure phyllodulcin. The samples were stored at 40° C. in closed glass vessels to prevent evaporation. The phyllodulcin contents of the test solutions are plotted against time in FIG. 1.

As can clearly be seen from FIG. 1, pure phyllodulcin is decomposed more rapidly than a comparable quantity of phyllodulcin in the form of an extract according to the invention. In a rough estimation, the stability is approximately tripled.

Example 3: Production of an Ethyl Acetate *Hydrangea dulcis* Dry Extract 2 g of dried fermented plant material (produced as described in Example 1) were extracted in 50 ml of ethyl acetate for one hour at 40° C. with stirring. The solvent was removed under vacuum and the dried extract was tasted in a dose of 55 ppm on sugar solution (5%) and assessed sensorially.

| Solvent | Yield | Content of phyllodulcin (based on dry mass) | Sensory assessment |
| --- | --- | --- | --- |
| Ethyl acetate | 0.1 mg | 14.4% | Herby, sweet, similar to sweetener |

Example 4: Production of an Ethanolic/Aqueous *Hydrangea dulcis* Dry Extract 2 g of dried fermented plant material (produced as described in Example 1) were extracted in 50 ml of ethanol/water (7:3) for one hour at room temperature with stirring. The solvent was removed under vacuum and the dried extract was tasted in a dose of 145 ppm on sugar solution (5%) and assessed sensorially.

| Solvent | Yield | Content of phyllodulcin (based on dry mass) | Sensory assessment |
| --- | --- | --- | --- |
| Ethanol/water (v/v 7:3) | 0.52 g | 5.3% | Sweet, relatively neutral |

Example 5: Production of an Aqueous/Ethanolic Ethyl Acetate *Hydrangea Dulcis* Dry Extract 2 g of dried fermented plant material (produced as described in Example 1) were extracted in 50 ml of water/ethanol (1:1) for one hour at 40° C. with stirring. The solvent was removed under vacuum and the dried extract was tasted in a dose of 240 ppm on sugar solution (5%) and assessed sensorially.

| Solvent | Yield | Content of phyllodulcin (based on dry mass) | Sensory assessment |
|---|---|---|---|
| Water/ethanol (v/v 1:1) | 0.52 g | 3.2% | Sweet, honey |

Application Example 1: Sweetness Enhancement Using *Hydrangea dulcis* Extracts Preliminary Test: Inherent Sweetness of the Extract The inherent sweetness of the extract from Example 2 (containing 7.2% by weight of phyllodulcin, based on dry mass) which was dissolved in different concentrations in pure form in water (0.0010, 0.0025, 0.0050, 0.0100, 0.0250, 0.0500% by weight in water) was determined using a comparative series of different sucrose concentrations in water (0, 0.25, 0.5, 0.75, 1, 1.5, 2, 3, 4 and 5% by weight sucrose in water). The panelists were requested to test and grade each individual extract solution compared to the sucrose series (sucrose equivalence). The inherent sweetness of the extract for the concentrations mentioned above could be determined from the results obtained from the panelists.

| Concentration of the extract from Example 2 in water [% by weight] | Phyllodulcin concentration in ppm | Determination of the sucrose equivalence in water | Other sensory description |
|---|---|---|---|
| 0.0010 | 0.7 | 0.2% | Tea note |
| 0.0025 | 1.75 | 0.45% | Tea note, hay |
| 0.0050 | 3.5 | 0.64% | Green tea |
| 0.0100 | 7 | 0.83% | Fennel, aniseed, black tea, slightly bitter |
| 0.0250 | 17.5 | 1.78% | Strong tea note, green, fishy, slightly bitter |
| 0.0500 | 35 | 2.7 | Licorice root, fishy, astringent, tea, hay, bitter |

It can be seen by extrapolation from the Table that it is possible to achieve a sucrose equivalence of 1.5% with approximately 200 ppm of the extract (corresponding to approximately 15 ppm of phyllodulcin) and 1% with approximately 150 ppm of the extract (corresponding to approximately 10 ppm of phyllodulcin).

Enhancement of the Sweetness Sensation of a Sucrose Solution

In order to quantify the enhancement of the sweetness sensation, the sweetness of a 5% sucrose solution and of a sample containing 5% of sucrose and an amount of the test substance or of the test extract, was determined by a group of experts (grade 1 [not sweet] to grade 10 [extremely sweet]). The evaluation was made as a calculation of the reduction (in %) of the sweetness sensation from the averages of the assessments of the sucrose solution or of the sucrose and the test substance or of the solution containing the test extract.

| Substance/extract | Extract concentration (ppm)/phyllodulcin concentration (ppm) | Sweetness sensation (1-10) without | Sweetness sensation (1-10) with | % Enhancement of the sweetness sensation |
|---|---|---|---|---|
| Ethanolic extract from Example 2 (contains 7.2% phyllodulcin) | 10/0.7 | 5.0 ± 0.8 | 5.4 ± 1.5 | 8% |
| ditto | 25/1.75 | 5.6 ± 1.2 | 5.9 ± 1.1 | 6% |
| ditto | 50/3.5 | 5.3 ± 1.3 | 6.9 ± 1.5 | 31% ($p < 0.01$) |
| ditto | 100/7 | 5.5 ± 0.9 | 7.4 ± 1.3 | 34% ($p < 0.001$) |
| ditto | 110/7.7 | 5.6 ± 1.7 | 7.5 ± 1.8 | 33% ($p < 0.01$) |
| ditto | 200/14 | 5.1 ± 0.8 | 7.6 ± 1.3 | 49% ($p < 0.001$) |
| Ethyl acetate extract from Example 3 (contains 14.4% phyllodulcin) | 55/7.7 | 4.9 ± 1.1 | 6.9 ± 1.3 | 42% ($p < 0.001$) |
| Ethanolic/aqueous extract from Example 4 (contains 5.3% phyllodulcin) | 145/7.7 | 5.3 ± 1.6 | 6.9 ± 1.5 | 30% ($p < 0.01$) |
| Ethanolic/aqueous extract from Example 5 (contains 3.2% phyllodulcin) | 240/7.7 | 5.3 ± 1.1 | 7.6 ± 1.6 | 43% ($p < 0.001$) |

It is possible to detect a very good sweetness enhancement even with the concentration of approximately 100 ppm ethanolic extract, which is not sweet per se, from Example 2, corresponding to less than 10 ppm of phyllodulcin. Purely by way of calculation, it would be expected that a 5% sucrose solution (corresponds sensorially by definition to 5% sucrose equivalents) which contains 100 ppm of ethanolic extract from Example 2, would produce additively a sweetness of approximately 5.8 sucrose equivalents. However, the sensory assessment of a mixed solution of this type of 5% sucrose with 100 ppm of the extract according to the invention from Example 2 produced by the method described in the preliminary test, a sucrose equivalence of 7.7%, which corresponds to a synergy of more than 30% above the expected value.

Application Example 2: Reduced-Sugar Soft Drink

Preparation A: comparative preparation with 10% sugar
Preparation B: comparative preparation with 8% sugar
Preparation C: comparative preparation with 8% sugar and neohesperidin dihydochalcone
Preparations D-H: reduced-sugar preparations according to the invention with 8% sugar

|  | Use in % by weight Preparation | | | | | | | |
|---|---|---|---|---|---|---|---|---|
| Ingredient | A | B | C | D | E | F | G | H |
| Sugar | 10 | 8 | 8 | 8 | 8 | 8 | 8 | 8 |
| Citric acid | 0.15 | 0.15 | 0.15 | 0.15 | 0.15 | 0.15 | 0.15 | 0.15 |
| Lemon flavoring | 0.1 | 0.1 | 0.1 | 0.1 | 0.1 | 0.1 | 0.1 | 0.1 |
| Neohesperidin-dihydrochalcone | — | — | 0.0001 | — | — | — | — | — |
| Extract from Example 2, containing 7% phyllodulcin | — | — | — | 0.011 | 0.005 | 0.005 | 0.005 | 0.005 |
| Phloretin | — | — | — | — | — | — | 0.002 | — |
| Hesperetin | — | — | — | — | — | — | — | 0.001 |
| Extract of *Rubus suavissimus*, containing 5% by weight rubusoside based on the total weight of the extract | — | — | — | — | — | 0.010 | — | — |
| Water | Make up to 100 | | | | | | | |

The ingredients were mixed in the stated sequence and made up to 100% with water. The mixtures were poured into glass bottles and carbonized.

The preparations were tested sensorially in blind duo tests. In this respect, the sweetness was assessed by experts using a grading of 1 [not sweet to 10 [extremely sweet].

| Comparison Between 1st and 2nd samples | Sweetness sensation (1-10) | | | Significance (n.s. = not significant) |
|---|---|---|---|---|
|  | 1st sample | 2nd sample | Change (%) |  |
| A and B | 7.1 ± 1.4 | 4.6 ± 1.3 | −36% | p < 0.001 |
| A and C | 6.3 ± 1.2 | 4.6 ± 1.9 | −28% | p < 0.01 |
| A and D | 6.9 ± 1.4 | 7.0 ± 1.5 | 2% | n.s. |
| A and E | 6.8 ± 1.8 | 5.9 ± 1.9 | −13% | n.s. |
| A and F | 5.4 ± 1.3 | 5.9 ± 1.4 | 9% | n.s. |
| A and G | 6.8 ± 1.5 | 6.3 ± 1.8 | −7% | n.s. |
| A and H | 6.8 ± 1.9 | 6.4 ± 2.2 | −6% | n.s. |

By omitting sugar (20% by weight, based on sucrose), a reduction in sweetness of approximately 36% was observed (preparations A and B).

As comparison (preparation C), the known sweetener neohesperidin dihydrochalcone was used in a concentration which alone in water corresponds to approximately 0.5% sucrose equivalence (determined by the method mentioned in Application example 1, first part). Compared to Comparative example A, the sweetness of the comparative preparation C, reduced in sugar by %, could not be reproduced alone by 1 ppm of neohesperidin dihydrochalcone.

By adding the extracts according to the invention on their own (preparations D and E) to the reduced-sugar preparation, the panelists were no longer able to detect any significant difference between the full sugar preparation and the relatively sugar-depleted preparation according to the invention (A as opposed to D or A as opposed to E); however, with the lower dosing (preparation E), it was still possible to detect a sweetness which was not completely reproduced.

This means that the extracts according to the invention are better able to reproduce the sweetness of reduced-sucrose applications than conventional sweeteners in low dosings of less than 1% sucrose equivalent.

However, by combining the lower dosing of 50 ppm of the extract of the invention according to Example 2 with known flavorings for sweetness enhancement (G, H), the sweetness could then be substantially reproduced or even more sweetness could be achieved by using extracts of *Rubus suavissimus* (F).

Application Example 3: Flavoring Mixtures, Containing Sweeteners

| Ingredient | Preparation (use in % by weight) | | | | | | | | |
|---|---|---|---|---|---|---|---|---|---|
|  | A | B | C | D | E | F | G | H | I |
| "Liquid sugar", contains 80% sucrose | 99.87 | — | — | — | — | — | — | — | — |
| Rebaudioside A 98% | — | 80 | — | — | 70 | 70 | 60 | 70 | 73.5 |
| Rebaudioside A 90% | — | — | 90 | — | — | — | — | — | — |
| Stevioside 95% | — | — | — | 75 | — | — | — | — | — |
| Extract of *Hydrangea dulcis* according to Example 2 (ethanolic, 7.7% phyllodulcin) | 0.10 | 20 | — | 20 | 20 | 10 | 10 | 20 | 20 |
| Extract of *Hydrangea dulcis* according to Example 3 (ethyl acetate, 14.4% phyllodulcin) | — | — | 10 | — | — | — | — | — | — |

-continued

| Ingredient | Preparation (use in % by weight) | | | | | | | | |
|---|---|---|---|---|---|---|---|---|---|
| | A | B | C | D | E | F | G | H | I |
| Extract of *Rubus suavissimus*, containing 5% by weight rubusoside, e.g. from plant extract | — | — | — | — | — | — | 25 | — | — |
| Phloretin | 0.02 | — | — | 4 | 5 | 3.2 | 3.5 | 5 | 5 |
| Hesperetin | 0.01 | — | — | 1 | 5 | 0.8 | 1 | 4.9 | 1 |
| Neohesperidin-dihydrochalcone | — | — | — | — | — | — | 0.5 | — | — |
| Homoeriodictyol-sodium salt | — | — | — | — | — | 16 | — | — | — |
| Vanillin, natural | — | — | — | — | — | — | — | 0.1 | — |
| Sugar distillate from cane sugar (e.g. Treatt) | — | — | — | — | — | — | — | — | 0.5 |

The substances or solutions are mixed in the proportions stated above and are used thus. The typical dosing of preparation A in the finished product is from 7 to 15% by weight, based on the finished product; the typical dosing of preparations B to I is from 0.01 to 0.1, based on the finished product, and preferably from 0.03 to 0.06%.

Application Example 4: Spray-Dried Preparation as Semi-Finished Product for the Flavoring of Finished Products

| Ingredient | Use in % by weight Preparation | | | | | | | | |
|---|---|---|---|---|---|---|---|---|---|
| | A | B | C | D | E | F | G | H | I |
| Drinking water | 60 | 60 | 60 | 60 | 60 | 60 | 60 | 60 | 60 |
| Maltodextrin from wheat | 10 | 25 | 25 | 25 | 25 | 25 | 25 | 25 | 25 |
| Gum arabic | 5 | 5 | 5 | 5 | 5 | 10 | 10 | 10 | 10 |
| Flavoring mixture A from Application example 3 | 25 | — | — | — | — | — | — | — | — |
| Flavoring mixture B from Application example 3 | — | 10 | — | — | — | — | — | — | — |
| Flavoring mixture C from Application example 3 | — | — | 10 | — | — | — | — | — | — |
| Flavoring mixture D from Application example 3 | — | — | — | 10 | — | — | — | — | — |
| Flavoring mixture E from Application example 3 | — | — | — | — | 10 | — | — | — | — |
| Flavoring mixture F from Application example 3 | — | — | — | — | — | 5 | — | — | — |
| Flavoring mixture G from Application example 3 | — | — | — | — | — | — | 5 | — | — |
| Flavoring mixture H from Application example 3 | — | — | — | — | — | — | — | 5 | — |
| Flavoring mixture I from Application example 3 | — | — | — | — | — | — | — | — | 5 |

The drinking water is introduced into a container and the maltodextrin and gum arabic are dissolved therein. The flavoring mixtures are then emulsified into the carrier solution using a Turrax. The temperature of the spray solution should not exceed 30° C. The mixture is then spray-dried (set temperature at inlet 185-195° C., set temperature at outlet: 70-75° C.).

Application Example 5: Solutions of the Flavoring Mixtures

The compositions of Application example 3 can also be taken up with water, propylene glycol, glycerol or ethanol or preferably with mixtures of the aforementioned solvents (for example water-propylene glycol, water-glycerol, water-ethanol, glycerol-ethanol, glycerol-propylene glycol, propylene glycol-ethanol) for example as a 1-20% solution, preferably a 2-20% solution, more preferably a 5% solution and are completely dissolved by gentle heating.

Application Example 6: "Cola"-Type Soft Drink

| Ingredient | Preparation (use in % by weight) | | | | | | | |
|---|---|---|---|---|---|---|---|---|
| | A | B | C | D | E | F | G | H |
| Saccharose | 0 | 8 | 7 | 7 | 7 | — | 7 | — |
| Glucose/fructose corn syrup, containing 55% by weight of fructose | — | — | — | — | — | 8 | — | 7 |
| Flavoring mixture A from Application example 3 | 10 | — | — | — | — | — | — | — |
| Flavoring mixture B from Application example 3 | — | 0.05 | — | — | — | — | — | — |
| Flavoring mixture C from Application example 3 | — | — | 0.05 | — | — | — | — | — |
| Flavoring mixture D from Application example 3 | — | — | — | 0.05 | — | — | — | — |

-continued

| Ingredient | Preparation (use in % by weight) | | | | | | | |
|---|---|---|---|---|---|---|---|---|
| | A | B | C | D | E | F | G | H |
| Flavoring mixture E from Application example 3 | — | — | — | — | 0.05 | — | — | — |
| Flavoring mixture F from Application example 3 | — | — | — | — | — | 0.05 | — | — |
| Flavoring mixture G from Application example 3 | — | — | — | — | — | — | 0.05 | — |
| Flavoring mixture I from Application example 3 | — | — | — | — | — | — | — | 0.05 |
| Phosphoric acid | 0.07 | 0.07 | 0.07 | 0.07 | 0.07 | 0.07 | 0.07 | 0.07 |
| Citric acid | 0.06 | 0.06 | 0.06 | 0.06 | 0.06 | 0.06 | 0.06 | 0.06 |
| Caramel | 0.14 | 0.14 | 0.14 | 0.14 | 0.14 | 0.14 | 0.14 | 0.14 |
| Caffeine | 0.01 | 0.01 | 0.01 | 0.01 | 0.01 | 0.01 | 0.01 | 0.01 |
| „Cola"-type emulsion drink | 0.05 | 0.05 | 0.05 | 0.05 | 0.05 | 0.05 | 0.05 | 0.05 |
| Water | Make up to 100% | | | | | | | |

The ingredients were mixed in the stated sequence, poured into bottles and carbonized.

Application Example 7: Iced Tea Drink

| Ingredient | Preparation (use in % by weight) | | | | | | | |
|---|---|---|---|---|---|---|---|---|
| | A | B | C | D | E | F | G | H |
| Flavoring mixture A from Application example 3 | 6 | — | — | — | — | — | — | — |
| Flavoring mixture F from Application example 3 | — | — | — | 0.03 | — | — | 0.03 | 0.03 |
| Flavoring mixture G from Application example 3 | — | 0.03 | — | — | 0.03 | — | — | — |
| Flavoring mixture H from Application example 3 | — | — | 0.03 | — | — | 0.03 | — | — |
| Citric acid | 0.15 | 0.12 | 0.15 | 0.12 | 0.15 | 0.12 | 0.15 | 0.12 |
| Ascorbic acid | 0.02 | 0.02 | 0.02 | 0.02 | 0.02 | 0.02 | 0.02 | 0.02 |
| Black tea extract | 0.15 | 0.15 | — | — | 0.15 | 0.15 | — | — |
| Green tea extract (at least 50% polyphenols) | — | — | 0.1 | 0.1 | — | — | 0.33 | 0.33 |
| "Lemon"-type natural flavoring | 0.1 | — | 0.1 | — | 0.1 | — | 0.1 | — |
| "Peach"-type natural flavoring | — | 0.07 | — | 0.07 | — | 0.07 | — | 0.07 |
| Water | Make up to 100% | | | | | | | |

The ingredients were mixed in the stated sequence, poured into bottles and sterilized.

Application Example 8: Use in a Chewing Gum

| Part | Ingredient | Use in % by weight |
|---|---|---|
| A | Chewing gum base, Company "Jagum T" | 30.00 |
| B | Sorbitol, pulverised | 38.975 |
| | Isomalt ® (Palatinit GmbH) | 9.50 |
| | Xylitol | 2.00 |
| | Mannitol | 3.00 |
| | Rebaudioside A 98% | 0.20 |
| | Ethanolic extract from Example 2 | 0.02 |
| | Hesperetin | 0.005 |
| | Emulgum ® (Colloides Naturels, Inc.) | 0.30 |
| C | Sorbitol, 70% | 14.00 |
| | Glycerol | 1.00 |
| D | Mint flavoring | 1 |

Parts A to D are mixed and kneaded intensively. The raw mass can be processed into ready-for-use chewing gum, for example as thin strips.

Application Example 9: Sugar-Free Hard Caramels

| Ingredient | Content (%) | | | |
|---|---|---|---|---|
| | A | B | C | D |
| Palatinite, type M | 75.00 | 74.00 | 75.50 | 75.00 |
| Citric acid | — | 1.0 | 0.5 | — |
| Water | 24.88 | 24.842 | 23.88 | 24.844 |
| Yellow coloring | — | 0.01 | — | — |
| Red coloring | — | — | 0.01 | — |
| Blue coloring | 0.01 | — | — | 0.01 |
| Peppermint flavoring | 0.1 | — | — | 0.1 |
| Lemon flavoring | — | 0.1 | — | — |
| Red fruit flavoring | — | — | 0.1 | — |
| Rebaudioside A 98% | — | 0.040 | — | 0.040 |
| Extract from Example 2 | 0.010 | 0.005 | 0.010 | 0.005 |
| Hesperetin | — | 0.001 | — | 0.001 |
| Phloretin | — | 0.002 | — | — |

Palatinite was mixed with water optionally after the addition of citric acid and the mixture was melted at 165° C. and then cooled to 115° C. The flavoring and the other ingredients were added and after being thoroughly mixed, the mixture was poured into moulds, removed from the moulds after solidifying and then packaged individually.

Application Example 10: Reduced-Sugar Steamed Pudding

Preparation A, B: comparative preparations with full sugar content (A) and reduced sugar content (B)

| | Preparation (amounts as % by weight) | | | | | |
|---|---|---|---|---|---|---|
| Ingredient | A | B | C | D | E | F |
| Sucrose | 7.8% | 5.4% | 5.4% | 5.4% | 5.4% | 5.4% |
| Starch | 3.0% | 3.0% | 3.0% | 3.0% | 3.0% | 3.0% |
| Skimmed milk powder | 1.5% | 1.5% | 1.5% | 1.5% | 1.5% | 1.5% |
| Aubygel MR50 | 0.5% | 0.5% | 0.5% | 0.5% | 0.5% | 0.5% |
| Vanilla bean extract, spray-dried, Symrise | 0.1% | 0.1% | 0.1% | 0.1% | 0.1% | 0.1% |
| Extract from Example 2 | — | — | 0.01% | 0.005% | 0.005% | 0.005% |
| Extract of Rubus suavissimus, containing 5% by weight rubusoside, e.g. from plant extract | — | — | — | — | 0.010% | 0.005% |
| Hesperetin | — | — | — | 0.001% | — | 0.001% |
| Phloretin | — | — | — | 0.002% | — | 0.002% |
| Milk 1.5% fat content | Make up to 100% | | | | | |

The solids were introduced and stirred up with the milk. The mixture was heated to 95° C. for 2 minutes with thorough stirring, decanted and cooled to 5-8° C.

Application Example 11: Low-Fat Yoghurts

Comparative Preparation with Sugar (A)
Preparations according to the invention with sweetener mixture and extract from Example 2 (B-D)

| | Preparation (amounts as % by weight) | | | |
|---|---|---|---|---|
| Ingredient | A | B | C | D |
| Sucrose | 10 | 8 | 6 | — |
| Rebaudioside A 98% | — | — | — | 0.050 |
| Extract from Example 2 | — | 0.010 | 0.005 | 0.010 |
| Extract of Rubus suavissimus, containing 5% by weight rubusoside, e.g. from plant extract | — | — | 0.010 | — |
| Hesperetin | — | 0.001 | 0.001 | 0.001 |
| Phloretin | — | — | 0.002 | — |
| Homoeriodictyol sodium salt | — | — | — | 0.005 |
| Yoghurt 0.1% fat | Make up to 100% | | | |

The ingredients were mixed and cooled at 5° C.

Application Example 12: Mixed Milk Drinks

Comparative Preparations with Sugar (A)
Preparations According to the Invention (B-D)

| | Preparation (amounts as % by weight) | | | |
|---|---|---|---|---|
| Ingredient | A | B | C | D |
| Sucrose | 10 | 8 | 7 | — |
| Fructose | — | — | 0.5 | — |
| Rebaudioside A 98% | — | — | — | 0.040 |
| Extract from Example 2 | — | 0.010 | 0.005 | 0.010 |
| Extract of Rubus suavissimus, containing 5% by weight rubusoside, e.g. from plant extract | — | — | 0.010 | — |
| Hesperetin | — | 0.003 | 0.002 | 0.005 |
| Phloretin | — | — | 0.002 | — |
| Homoeriodictyol sodium salt | — | — | — | 0.002 |
| UHT milk, 1.5% fat | Make up to 100% | | | |

The ingredients were mixed, made up with milk, stirred thoroughly, poured into bottles and stored, chilled, at 5° C.

Application Example 13: Reduced-Sugar Tomato Ketchup

Comparative Preparation with Sugar (A)
Comparative Preparation with Reduced Sugar Content (B)
Preparations According to the Invention (C-I)

| | Preparation (amounts as % by weight) | | | | | | | |
|---|---|---|---|---|---|---|---|---|
| Ingredient | A | B | C | E | F | G | H | I |
| Common salt | 2 | 2 | 2 | 2 | 2 | 2 | 2 | 2 |
| Starch, Farinex WM 55 | 1 | 1 | 1 | 1 | 1 | 1 | 1 | 1 |
| Sucrose | 12 | 9.6 | 9.2 | 8.4 | 9.6 | 9.6 | 8.4 | 4.2 |
| Tomato concentrate × 2 | 40 | 40 | 40 | 40 | 30 | 30 | 30 | 30 |
| Glucose syrup 80 Brix | 18 | 18 | 18 | 18 | 18 | 18 | 18 | 18 |
| Spirit vinegar 10% | 7 | 7 | 7 | 7 | 3 | 3 | 3 | 3 |
| Rebaudioside A 98% | — | — | — | — | — | — | — | 0.05 |
| Extract from Example 2 | — | — | 0.01 | 0.005 | 0.005 | 0.01 | 0.005 | 0.01 |

-continued

| Ingredient | Preparation (amounts as % by weight) | | | | | | | |
|---|---|---|---|---|---|---|---|---|
| | A | B | C | E | F | G | H | I |
| Extract of *Rubus suavissimus*, containing 5% by weight rubusoside, e.g. from plant extract | — | — | — | — | — | — | 0.01 | — |
| Hesperetin 2.5% in 1,2-propylene glycol | — | — | — | — | 0.1 | — | 0.1 | — |
| Phloretin 2.5% in 1,2-propylene glycol | — | — | — | 0.2 | 0.2 | — | — | 0.3 |
| Water | Make up to 100% | | | | | | | |

The ingredients are mixed in the stated sequence and the finished ketchup is homogenized using an agitator, poured into bottles and sterilized.

Application Example 14: Reduced-Sugar Ice Cream

Comparative Preparation with Sugar (A)
Comparative Preparation with Reduced Sugar Content (B)
Preparations According to the Invention (C-F)

| Ingredient | Preparation (content in % by weight) | | | | | |
|---|---|---|---|---|---|---|
| | A | B | C | D | E | F |
| Vegetable fat, melting range 35-40° C. | 20.00 | 20.00 | 20.00 | 20.00 | 20.00 | 20.00 |
| Sugar (Saccharose) | 12.00 | 8.00 | 8.00 | 8.00 | 8.00 | 8.00 |
| Skimmed milk powder | 5.00 | 5.00 | 5.00 | 5.00 | 5.00 | 5.00 |
| Glucose syrup 72% dry matter | 5.00 | 5.00 | 5.00 | 5.00 | 5.00 | 5.00 |
| Emulsifier SE 30 (Grindstedt Products, Denmark) | 0.65 | 0.65 | 0.65 | 0.65 | 0.65 | 0.65 |
| Flavoring, containing 0.1% diacetyl and 1% vanillin | 0.20 | 0.20 | 0.20 | 0.20 | 0.20 | 0.20 |
| Extract from Example 2 | — | — | 0.01 | 0.005 | 0.01 | 0.005 |
| Extract of *Rubus suavissimus*, containing 5% by weight rubusoside, e.g. from plant extract | — | — | — | — | — | 0.010 |
| Hesperetin 2.5% in 1,2-propylene glycol | — | — | — | 0.10 | — | 0.10 |
| Phloretin 2.5% in 1,2-propylene glycol | — | — | — | — | 0.05 | 0.05 |
| Skimmed milk | Make up to 100% | | | | | |

The vegetable fat was heated to 58° C. Skimmed milk and glucose syrup were heated to 55° C. and sugar, skimmed milk powder as well as emulsifier and flavoring were added and the mixture was introduced into the vegetable fat. The mixture was homogenized using a through-flow high-pressure homogenizer (180/50 bar). The resulting mass was tempered for 1 minute at 78° C., then cooled to 2-4° C. and incubated at this temperature for 10 hrs for maturing. The matured mass was then filled into containers and stored frozen at −18° C.

Application Example 15: Ice Cream Suitable for Diabetics

An ice cream suitable for diabetics was prepared from the following ingredients and filled into 95 ml portion tubs:
concentrated, skimmed milk, fructose syrup, strawberry pieces and strawberry puree (15%), vegetable fat, diet chocolate chips (3.5% with soya lecithin emulsifier), whey product, beetroot juice, locust bean gum, guar gum, carrageen, emulsifier (E 471), gelatin, acidifying agent citric acid, 0.1% strawberry flavoring (containing 1% by weight of the extract from Example 2 and 1% by weight of phloretin), based on the total weight of the strawberry flavoring), carotene coloring.

Nutritional Value (Per 95 ml):
Protein 1.8 g, carbohydrates 13.3 g (of which fructose 9.5 g), fat 4.2 g.

Application Example 16: Diet Chocolate Based on Maltitol

A chocolate suitable for diabetics was prepared from the following ingredients and poured into rectangular bars:
maltitol, hazelnut mass, cocoa butter, skimmed milk powder, cocoa mass, inulin, concentrated butter, emulsifier soya lecithins, 0.1% vanilla flavoring (containing vanilla bean extract, vanillin and 1% by weight of the extract from Example 2 and 0.3% by weight of hesperetin, based on the total weight of the vanilla flavoring).

Nutritional Value (Per 100 g):
Protein 8 g, carbohydrates 43 g (of which maltitol 34 g), fat 34 g.

Application Example 17: Diet Chocolate Based on Fructose

A chocolate suitable for diabetics was prepared from the following ingredients and poured into rectangular bars:
cocoa mass, fructose, skimmed milk powder, cocoa butter, inulin, concentrated butter, emulsifier soya lecithin, walnuts, cooking salt, 0.1% vanilla flavoring (containing vanillin and 1% by weight of the extract from Example 2 and 0.2% by weight of hesperetin and 1% by weight of homoeriodictyol sodium salt, based on the total weight of the vanilla flavoring).

Nutritional Value (Per 100 g):

Protein 8.8 g, carbohydrates 34 g (of which fructose 23 g, lactose 7.5 g, saccharose 1.4 g), fat 36 g; dietary fiber 18.5 (of which 12.2 g inulin); sodium: 0.10 g. Cocoa content at least 50% by weight.

Application Example 18: Reduced-Sugar Musli Mixture

| Ingredient | Preparation (content in % by weight) | |
|---|---|---|
| | A | B |
| Oat flakes | 17.00 | 18.90 |
| Crunchy oat flake clusters | 10.00 | 12.00 |
| Rice Crispies | 16.90 | 17.80 |
| Cornflakes | 16.50 | 17.50 |
| Currants | 3.50 | 3.50 |
| Hazelnuts, chopped | 2.50 | 2.50 |
| Glucose syrup from wheat, DE 30 | 9.50 | 9.50 |
| Saccharose | 20.00 | 14.00 |
| Water | 4.00 | 4.00 |
| Citric acid powder, anhydrous | 0.10 | 0.10 |
| Flavoring, containing 1% by weight of extract from Example 2 and 0.1% hesperetin, based on the flavoring | — | 0.20 |

Ingredients Nos. 1 to 6 are mixed in each case in a rotary drum (Mix 1). Ingredients Nos. 7 to 9 are each heated and ingredient No. 10 (in recipe B also ingredient No. 11) is added (Mix 2). Mix 2 is added to Mix 1 and then they are thoroughly mixed together. Finally, the resulting muesli mixture is turned out onto a baking tray and dried in an oven for 8 minutes at 130° C.

Application Example 19: Reduced-Sugar Fruit Gums

| Ingredient | Preparation (content in % by weight) | |
|---|---|---|
| | A | B |
| Water | 23.70 | 25.70 |
| Saccharose | 34.50 | 8.20 |
| Glucose syrup, DE 40 | 31.89 | 30.09 |
| Iso Syrup C* Tru Sweet 01750 (Cerestar GmbH) | 1.50 | 2.10 |
| Gelatine 240 Bloom | 8.20 | 9.40 |
| Polydextrose (Litesse ® Ultra, Danisco Cultor GmbH) | — | 24.40 |
| Yellow and red colorings | 0.01 | 0.01 |
| Citric acid | 0.20 | 0.20 |
| Cherry flavoring, containing 1% by weight of extract from Example 2 and 0.3% by weight of phloretin, based on the flavoring | — | 0.10 |

Polydextrose is itself a non-sweet-tasting polysaccharide with a low calorific value.

Application Example 20: Choco-Cappuccino Ice Cream

| Ingredient | Preparation (content in % by weight) | |
|---|---|---|
| | A | B |
| Glucose-fructose syrup | 14.10 | 14.10 |
| Saccharose | 10.00 | 7.50 |
| Skimmed milk powder | 5.00 | 5.00 |
| Cream (36% fat content) | 24.00 | 24.00 |
| Emulsifier and stabilizer Cremodan ® 709VEG (Danisco) | 0.50 | 0.50 |
| Cocoa powder | 5.975 | 5.975 |
| Carrageenan | 0.025 | 0.025 |
| Water | 40.20 | 42.50 |
| Cappuccino flavoring | 0.20 | 0.20 |
| Containing 1% by weight of extract from Example 2 and 1% by weight of homoeriodictyol sodium salt, based on the flavoring | — | 0.20 |

Application Example 21: Gelatin Capsules for Direct Consumption

| Ingredient | Preparation (content in % by weight) | | |
|---|---|---|---|
| | A | B | C |
| Gelatin sheath: | | | |
| Glycerin | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |
| Core composition: | | | |
| Vegetable oil-triglyceride (coconut oil fraction) | 79.55 | 68.70 | 58.95 |
| Orange flavoring containing 1% by weight of extract from Example 2 and 1% by weight of homoeriodictyol sodium salt, based on the flavoring | 10.0 | 20.0 | 28.65 |
| Rebaudioside A 98% | 0.05 | 0.05 | — |
| 2-hydroxypropyl-menthylcarbonate | 0.33 | 0.20 | — |
| 2-hydroxyethylmenthyl-carbonate | — | 0.20 | 1.00 |
| (1R,3R,4S) menthyl-3-carboxylic acid-N-ethylamide (WS-3) | — | 0.55 | 0.50 |
| (−)-Menthone glycerin acetal (Frescolat MGA) | — | 0.30 | 0.80 |
| Vanillin | 0.07 | — | 0.10 |

The gelatin capsules suitable for direct consumption were prepared according to WO 2004/050069 and had a diameter of 5 mm and the weight ratio of core material to sheath material was 90:10. The capsules opened in the mouth in less than 10 seconds and dissolved completely in less than 50 seconds.

The invention claimed is:
1. A flavoring mixture comprising:
(i) sucrose;
(ii) phyllodulcin and/or a salt thereof; and
(iii) hydrangenol and/or a salt thereof;

wherein a ratio of a sucrose equivalence of a concentration of the sucrose of (i) to a sucrose equivalence of a concentration of the phyllodulcin and/or salt of (ii) is ≥4, and the flavoring mixture synergistically enhances the sweetness of an aqueous composition comprising the flavoring mixture in comparison to an otherwise identical aqueous composition without the phyllodulcin and/or salt of (ii).

2. The flavoring mixture of claim 1, further comprising:
(iv) at least one substance selected from the group consisting of a flavoring, an aromatic substance which enhances a sweet taste, and a physiologically compatible salt thereof.

3. The flavoring mixture of claim 1, further comprising at least one naturally occurring sweet-tasting substance selected from the group consisting of:
a) carbohydrates selected from the subgroup consisting of trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-gyceraldehyde and maltodextrin;
b) naturally occurring sugar alcohols selected from the subgroup consisting of glycerol, erythritol, threitol, arabitol, ribitol, xylitol, sorbitol, mannitol, maltitol, isomaltitol, dulcitol, and lactitol;
c) naturally occurring sweeteners, selected from the subgroup consisting of miraculin, curculin, monellin, mabinlin, thaumatin, curculin, brazzein, pentadin, D-phenylalanine and D-tryptophan;
d) naturally occurring sweeteners, selected from the subgroup consisting of stevioside, steviolbioside, rebaudioside A, further stevilglycosides selected from rebaudioside B, rebaudioside C, rebaudioside D, rebaudioside E, rebaudioside F, rebaudioside G, rebaudioside H, dulcoside and/or rubusoside, oslandin, polypodoside A, strogin 1, strogin, 2 strogin 4, selligueanin A, dihydroquercetin-3-acetate, perillartin, telosmoside A15, periandrin I-V, pterocaryosides, cyclocaryosides, mukuroziosides, trans-anethol, trans-cinnamaldehyde, bryosides, bryonosides, bryonodulcosides, carnosiflo sides, scandenosides, gypenosides, trilobatin, phloridzin, dihydroflavanols, hematoxylin, cyanin, chlorogenic acid, albiziasaponin, telosmosides, gaudichaudio side, mogrosides, hernandulcin and glycyrrhetinic acid;
e) a physiologically compatible, sweet-tasting derivative of the naturally occurring sweet-tasting substance of a) to d); and
f) a physiologically compatible salt of the substance or derivative of a) to e).

4. The flavoring mixture of claim 2, wherein the at least one substance of (iii) is selected from the group consisting of:
hesperetin,
phloretin,
3',7-dihydroxy-4'-methoxyflavan, and
(S)-3',7-dihydroxy-4'-methoxyflavan.

5. The flavoring mixture of claim 1, further comprising at least one flavoring, auxiliary, or carrier.

6. The flavoring mixture of claim 1, wherein the ratio of the sucrose equivalence of the concentration of the sucrose of (i) to the sucrose equivalence of the concentration of the phyllodulcin and/or salt of (ii) is ≥6.

7. An orally consumable product comprising the flavoring mixture of claim 1.

8. The orally consumable product of claim 6, wherein a concentration of the flavoring mixture is adjusted such that a concentration of the phyllodulcin and/or salt of (ii) is from 0.5 to 15 ppm, based on the weight of the orally consumable product.

9. The orally consumable product of claim 6 selected from the group consisting of a pharmaceutical preparation, an oral care preparation, a semi-finished product, a liquid, and a solid foodstuff.

10. A method for enhancing sweetness of an orally consumable product, the method comprising adding the flavoring mixture of claim 1 to the orally consumable product.

11. A flavoring mixture comprising
(i) sucrose; and
(ii) an extract of *Hydrangea Dulcis*, the extract comprising from 0.1 to 50 wt. % of phyllodulcin and/or a salt thereof and from 0.01 to 30 wt. % of hydrangenol and/or a salt thereof, wherein the weight percent of the phyllodulcin, hydrangenol, and salts thereof is based on the dry weight of the extract; and
wherein a ratio of a sucrose equivalence of a concentration of the sucrose of group (i) to a sucrose equivalence of a concentration of the phyllodulcin and/or salt of group (ii) is ≥4, and the flavoring mixture synergistically enhances the sweetness of an aqueous composition comprising the flavoring mixture in comparison to an otherwise identical aqueous composition without the extract of *Hydrangea Dulcis*.

12. The flavoring mixture of claim 11, further comprising
(iii) at least one substance selected from the group consisting of a flavoring, an aromatic substance which enhances a sweet taste, and a physiologically compatible salt thereof.

13. The flavoring mixture of claim 11, further comprising at least one naturally occurring sweet-tasting substance selected from the group consisting of:
a) carbohydrates selected from the subgroup consisting of trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-gyceraldehyde and maltodextrin;
b) naturally occurring sugar alcohols selected from the subgroup consisting of glycerol, erythritol, threitol, arabitol, ribitol, xylitol, sorbitol, mannitol, maltitol, isomaltitol, dulcitol, and lactitol;
c) naturally occurring sweeteners, selected from the subgroup consisting of miraculin, curculin, monellin, mabinlin, thaumatin, curculin, brazzein, pentadin, D-phenylalanine and D-tryptophan;
d) naturally occurring sweeteners, selected from the subgroup consisting of stevioside, steviolbioside, rebaudioside A, further stevilglycosides selected from rebaudioside B, rebaudioside C, rebaudioside D, rebaudioside E, rebaudioside F, rebaudioside G, rebaudioside H, dulcoside and/or rubusoside, oslandin, polypodoside A, strogin 1, strogin, 2 strogin 4, selligueanin A, dihydroquercetin-3-acetate, perillartin, telosmoside A15, periandrin I-V, pterocaryosides, cyclocaryosides, mukuroziosides, trans-anethol, trans-cinnamaldehyde, bryosides, bryonosides, bryonodulcosides, carnosiflo sides, scandenosides, gypenosides, trilobatin, phloridzin, dihydroflavanols, hematoxylin, cyanin, chlorogenic acid, albiziasaponin, telosmosides, gaudichaudio side, mogrosides, hernandulcin and glycyrrhetinic acid;

e) a physiologically compatible, sweet-tasting derivative of the naturally occurring sweet-tasting substance of subgroups a) to d); and
f) a physiologically compatible salt of the substance or derivative of subgroups a) to e).

14. The flavoring mixture of claim 12, wherein the at least one substance of (iii) is selected from the group consisting of
hesperetin,
phloretin,
3',7-dihydroxy-4'-methoxyflavan, and
(S)-3',7-dihydroxy-4'-methoxyflavan.

15. The flavoring mixture of claim 11, further comprising at least one flavoring, auxiliary, or carrier.

16. The flavoring mixture of claim 11, wherein the ratio of the sucrose equivalence of the concentration of the sucrose of group (i) to the sucrose equivalence of the concentration of the phyllodulcin and/or salt of (ii) is ≥6.

17. An orally consumable product comprising the flavoring mixture of claim 11.

18. The orally consumable product of claim 17, wherein a concentration of the flavoring mixture is adjusted such that a concentration of the phyllodulcin and/or salt of (ii) is from 0.5 to 15 ppm, based on the weight of the orally consumable product.

19. The orally consumable product of claim 16 selected from the group consisting of a pharmaceutical preparation, an oral care preparation, a semi-finished product, a liquid, and a solid foodstuff.

20. A method for enhancing sweetness of an orally consumable product, the method comprising adding the flavoring mixture of claim 11 to the orally consumable product.

* * * * *